United States Patent [19]

Parada et al.

[11] Patent Number: 6,071,709
[45] Date of Patent: Jun. 6, 2000

[54] NERVE GROWTH FACTOR/RECEPTOR COMPLEX

[75] Inventors: Luis F. Parada, Frederick, Md.; Dan Soppet, Springfield, Va.; David Kaplan, Middletown, Md.; Dionisio Martin-Zanca, Salamanca, Spain

[73] Assignee: The United States of America as represented by the Department of Health and Human Services, Washington, D.C.

[21] Appl. No.: 07/890,713

[22] Filed: May 29, 1992

Related U.S. Application Data

[63] Continuation-in-part of application No. 07/668,298, Mar. 14, 1991, Pat. No. 5,231,001.

[51] Int. Cl.$^7$ ................................................ G01N 33/567
[52] U.S. Cl. ......................... 435/7.21; 435/7.4; 435/15; 435/194; 436/536; 530/399
[58] Field of Search .................... 435/7.9, 7.21, 435/7.4, 15, 194; 436/536; 530/399

[56] References Cited

U.S. PATENT DOCUMENTS

| 5,231,001 | 7/1993 | Kaplan et al. ........................ | 435/7.21 |
| 5,622,862 | 4/1997 | Squinto et al. ........................ | 435/353 |

OTHER PUBLICATIONS

Klein et al., Cell 61: 647–656, 1990.
Klein et al., Cell 65: 189–197, 1991.
Soppet et al., Cell 65: 895–903, 1991.
Squinto et al., Cell 65: 885–893, 1991.
Kaplan et al. "Tyrosine Phosphorylation and Kinase Activity of the trk Proto–Oncongene Product Induced by NGF", *Nature*, 350(6314):158–160, 1991.
Klein et al. "trkB, a Novel Tyrosine Protein Kinase Receptor Expressed During Mouse Neural Development", *EMBO Journal*, 8(12):3701–3709, 1989.
Klein et al. "Expression of the Tyrosine Kinase Receptor Gene trkB in Confined to the Murine Embryonic . . . ", *Development*, 109:845–850, 1990.
Berg et al. *J. Biol. Chem.* 267(1): 13 (1992).
Hefti et al. "Neurotropic Strategies in Neurodegenerative Disease", UCLA Symposium on *Advances in Understanding Neurodegenerative Disorders*, Jan. 1992.

*Primary Examiner*—Donna C. Wortman
*Attorney, Agent, or Firm*—Needle & Rosenberg, P.C.

[57] ABSTRACT

The present invention relates to a complex comprising nerve growth factor (NGF) and trk proto-oncogene protein and a complex comprising neurotrophic factors, NT-3 or BDNF, and trkB proto-oncogene protein. The present invention also relates to methods for detecting the presence of NGF, NT-3 or BDNF neurotrophic factors and trk and trk-related proto-oncogene receptors. The present invention further relates to methods that may be used in diagnostics and therapeutics for neurodegenerative diseases such as Alzheimer's and Huntington's by detecting complexes comprising NGF or NGF related neurotrophic factors bound to the product of the tyrosine kinase trk or related trk proto-oncogene family member.

4 Claims, 16 Drawing Sheets

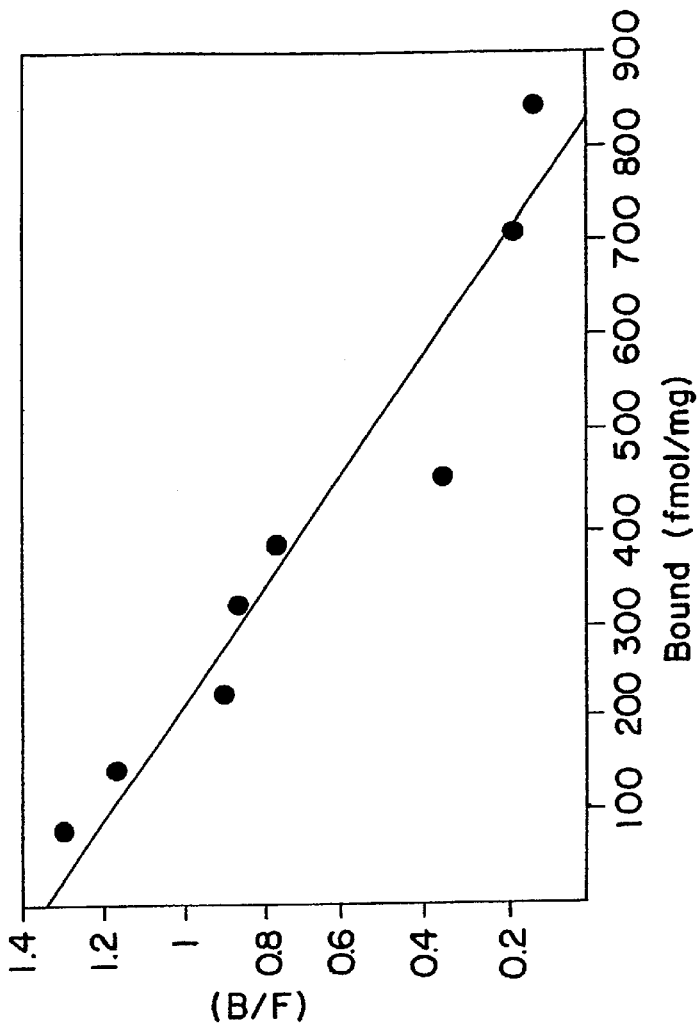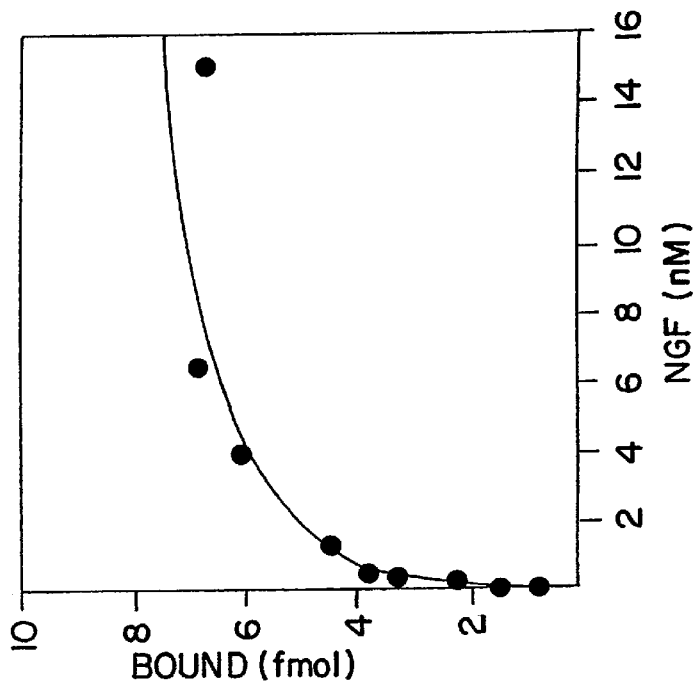

NERVE GROWTH FACTOR/RECEPTOR COMPLEX

This is a continuation-in-part of application Ser. No. 07/668,298 filed Mar. 14, 1991, now U.S. Pat. No. 5,231,001, the entire contents being hereby incorporated by reference.

BACKGROUND OF THE INVENTION

1. Field of the Invention

The present invention relates to a complex comprising the neurotrophic factor nerve growth factor (NGF) and trk-proto-oncogene protein receptor and a complex comprising the NGF related neurotrophic factors, neurotrophin-3 (NT-3) or brain-derived neurotrophic factor (BDNF) bound to trkB-proto-oncogene protein. The present invention also relates to a method of detecting the presence of NGF, NT-3 and BDNF ligands, and trk and trkB-proto-oncogene receptor proteins.

The present invention further relates to methods of diagnosing and treating conditions of nerve growth disease and regeneration such as Alzheimer's disease and neuroblastoma. In particular, the present method involves detection of the ligand-receptor pairs.

The present invention further relates to a method of detecting other neurotrophic factor receptor/ligand complexes on the basis of structural and functional relatedness to the trk receptor and NGF.

2. Background Information

The development of the vertebrate nervous system is characterized by a series of complex events beginning with an apparently homogeneous neuroepithelium in the early embryo and leading to formation of diverse, highly ordered, and interconnected neural cell types in the adult. Considerable descriptive and experimental evidence has been amassed which points to the existence of limiting diffusible factors that are required for the targeting, survival, and proper synaptic arrangement of neurons (R. W. Oppenheim, In: Studies in Developmental Neurobiology. (Cowan, W. M. ed.), Oxford University press, pp. 74–133, 1981; W. D. Snider and E. M. Johnson, *Ann. Neurol.* 26:489–506 (1989)). Functional neuronal circuits are sculpted from an initially overabundant production of neurons during development. In the mid term embryo, a process of programmed cell death eliminates a major proportion of the neuron population, leaving behind the appropriate number of neurons required for innervation of target tissues (V. Hamburger and R. Levi-Montalcini, *J. Exp. Zool.* 111:457–502 (1949); Y.-A. Barde, *Neuron* 2:1525–1535 (1989)).

The discovery of nerve growth factor (NGF) provided the first direct evidence for the existence of neurotrophic, polypeptide factors (R. Levi-Montalcini and V. Hamburger, *J. Exp. Zool.* 116:321–362 (1951); R. Levi-Montalcini and P. U. Angeletti, *Physiol. Rev.* 48:534–569 (1968)). This has been followed by the more recent description of additional neurotrophic factors: BDNF, ciliary neurotrophic factor (CTNF), and NT-3 (for review see W. D. Snider and E. M. Johnson, *Ann. Neurol.* 26:489–506 (1989); G. Barbin et al., *J. Neurochem.* 43:1468–1478 (1984); P. C. Maisonpierre et al., *Science* 247:1446–1451 (1990)). The physiological consequences elicited by NGF in vitro and in vivo have been at the center of research in neurobiology for several decades. Consequently, considerable information is now available about the cell types that respond to NGF in the peripheral and central nervous systems.

NGF is known to play a role in the targeting and survival of sympathetic and neural crest-derived sensory neurons as well as in selected populations of cholinergic neurons in the brain (L. A. Greene and E. M. Shooter, *Annu. Rev. Neurosci.* 3:353–402 (1980); H. Thoenen and Y.-A. Barde, *Physiol. Rev.* 60:1284–1335 (1980); H. Gnahn et al., *Dev. Brain. Res.* 9:45–52 (1983)). It appears that the NGF dependent cholinergic neurons in the basal forebrain correspond to the population of cells that undergo attrition in patients with Alzheimer's disease (F. Hefti, *Annals of Neurology,* 13:109–110 (1983); Hefti and Werner, (1986); Johnson and Tanuchi, (1987); P. J. Whitehouse et al., *Science* 215:1237–1239 (1982)). In vivo studies, in which NGF was injected in the periphery of the mouse embryo trunk, result in enhanced survival of sensory ganglia that are normally targeted for cell death (V. Hamburger et al., *J. Neurosci.* 1:60–71 (1981); I. B. Black et al., In: Growth Factors and Development, Current Topics in Developmental Biology, Vol. 24 (Nilsen-Hamilton, ed.), pp. 161–192 (1990)).

Exposure of embryos to NGF antibodies, that thereby partially neutralize the function of NGF, results in reduced survival of dorsal root ganglion neurons while injection of NGF antibodies into neonate mice has the principal effect of inhibiting the survival of sympathetic neurons (R. Levi-Montalcini and B. Booker, *Proc. Natl. Acad. Sci. USA,* 46:373–384 or 384–391 (1960); S. Cohen, *Proc. Natl. Acad. Sci. USA,* 46:302–311 (1960); E. M. Johnson et al., *Science* 210:916–918 (1980)).

In vitro, some tumor cell lines of neural origin respond to the presence of NGF by undergoing differentiation along neuronal pathways. PC12 cells, derived from a rat pheochromocytoma, are the best characterized of these cell lines and represent a widely accepted model for NGF-mediated response and for neuronal differentiation (L. A. Greene and A. S. Tischler, *Proc. Natl. Acad. Sci. USA* 73:2424–2428 (1976)).

Although much is understood about the biology of NGF outside the cell, the mechanisms by which NGF elicits neurotrophic effects within the cell have not been fully resolved. Interaction of NGF with a cell receptor is a requisite step in the transmission of neurotrophic signals within the cell (for review see M. V. Chao, In: Handbook of Experimental Pharmacology, Vol. 95/II Peptide Growth Factors and Their Receptors II (Sporn, M. B. and Roberts, A. B. eds.), Springer-Verlag, Heidelberg, pp. 135–165 (1990)).

A major advance in understanding NGF interactions with the cells was the identification and cloning of a 75 kDa receptor (75kNGF-R) that binds NGF, and is present in NGF-responsive cells. The clones of the gene encoding 75kNGF-R have been characterized from several species (M. V. Chao et al., *Science* 232:418–421 (1986); M. J. Radeke et al., *Nature* 325:593–597 (1987)). Unfortunately, the structural and biological properties of 75kNGF-R have provided limited clues about the nature of the NGF signal transduction pathway inside the cell. 75kNGF-R displays the binding properties of a low affinity NGF receptor ($Kd \approx 10^{-9}M$) when expressed in exogenous cell lines and analysis of the intracellular domain has not revealed putative domains of catalytic action (M. V. Chao, (1990)).

The biological responsiveness to NGF, however, is widely held to depend upon interactions with a high affinity binding component implying that other receptor or receptor subunits may be involved in NGF responses. The search for potential second messengers that might transmit NGF signals in PC12 cells has led to recent evidence indicating that activation of tyrosine kinases may represent an early response to the presence of NGF (Maher (1988)). These data implicate tyrosine kinases as candidates in the composition of a high affinity receptor.

Recent experiments suggest that the trk tyrosine kinase gene family fulfills this role (D. R. Kaplan et al., *Nature* 350:158–150 (1991a) and *Science* 252:554–558 (1991b); Hempstead et al., *Nature* 350:678–683 (1991); R. Klein et al., *Cell* 65:189–197 (1991)). The trk gene family is comprised of two well-characterized genes, trk and trkB (D. Martin-Zanca et al., *Nature* 319:743–748 (1986); R. Klein et al., *EMBO J.* 8:3701–3709 (1989), *Development* 4:845–850 (1990a) and *Cell* 61:647–656 (1990b); D. S. Middlemas et al., *Mol. Cell. Biol.* 11:143–153 (1991)), as well as additional uncharacterized members. The human trk oncogene was first identified in the NIH 3T3 transformation focus-forming assay, and other oncogenic alleles have been detected in human colon and papillary thyroid carcinomas (Martin-Zanca et al., (1986); Bongarzone et al., *Oncogene* 4:1457–1462, (1989)). Molecular cloning and sequencing analysis of the human proto-oncogene revealed a 790 amino acid open reading frame that displays all the recognizable features of a protein tyrosine kinase receptor molecule of 140 kd (gp $140^{proto-trk}$) (Martin-Zanca et al., (1986)). Applicants and others have cloned and studied the mouse trk proto-oncogene and found that expression of this gene is restricted primarily to subpopulations of sensory neural crest-derived neurons (Martin-Zanca et al., *Genes Dev.* 4:683–694 (1990)) and expression of the trk protein tyrosine kinase receptor gene family is limited exclusively to the murine embryonic and mature nervous system. (The Avian Model in Developmental Biology: From Organism to Genes, Editions du CNRS—pp. 291–302 (1990)). The expression profile seen for trk correlates, at least in part, with the location of specific neurons that depend on NGF for their survival.

The trkB gene also encodes a protein tyrosine kinase receptor that displays strong evolutionary conservation with trk. The respective tyrosine kinase domains share >88% amino acid homology. The extracellular ligand-binding domains also share homology (~40%), including conservation of all cystine residues, although some regions have diverged considerably (Klein et al., (1989)); Middlemas et al., (1991)).

In situ RNA expression studies have demonstrated that, like trk, trkB expression is primarily confined to tissues of the nervous system (Klein et al., (1989), (1990), (1990); Martin-Zanca et al., (1990)). However, additional features in the organization and transcription of the trkB gene depart considerably from those previously observed for the trk gene. trkB transcripts are widespread throughout the central and peripheral nervous systems and are not confined to neurons as they can also apparently be found in nonneuronal cells (such as glia and Schwann cells) (Klein et al., (1989) and (1990)). In contrast, trk gene expression is confined to a subpopulation of neural crest-derived sensory neurons in the peripheral nervous system (Martin-Zanca et al., (1990)) and in neurons of the basal forebrain and trigeminal mesencephalic nucleus. Furthermore, the trk gene apparently encodes only a single transcript (3.2 kb), while multiple transcripts ranging from 0.7 to 9.0 kb have been observed when mouse or rat brain mRNAs are hybridized with trkB probes (Klein et al., (1989) and (1990); Middlemas et al., (1991)). The quantity and location of the various-sized trkB transcripts are differentially regulated during embryonic development (Klein et al., (1990)).

Yet another departure between trk and trkB is that the trkB gene encodes at least two distinct molecules (Klein et al., (1990)). One trkB protein product is colinear with the trk receptor and constitutes a tyrosine kinase receptor glycoprotein of 145 kd (gp $145^{trkB}$). The second molecule is identical to gp $145^{trkB}$ in the extracellular and transmembrane domains (465 amino acids) but diverges in the intracellular region, lacking a catalytic tyrosine kinase domain and encoding a short cytoplasmic stretch of 23 amino acids; the predicted size of this form is 95 kd (the final 11 carboxy-terminal residues are unique to gp$95^{trkB}$ (Klein et al., (1990); Middlemas et al., (1991)). Anti-peptide antibodies generated against both forms of the trkB product have been used to demonstrate the existence of gp $145^{trkB}$ and gp$95^{trkB}$ in adult mouse brain (Klein et al., (1990)).

Cross-linking and binding experiments have been used to study the requisite interaction between neurotrophic factors and specific cell surface receptors (Chao, (1990)). Two binding affinities, one high, the other low, have been described for NGF (A. Sutter et al., *J. Biol. Chem.* 254:5972–5982 (1979)) and BDNF (A. Rodriguez-Tébar and Y.-A. Barde, *Nature* 8:3337–3342 (1988)) in sensory neurons, although the molecular nature of the high binding affinity has remained obscure. A cDNA encoding a 75 kd (gp$75^{NGFR}$) receptor that binds NGF at low affinity has been cloned (D. Johnson et al., *Cell* 47:545–554 (1986); Radeke et al., (1987)). The recent work of Kaplan et al., (1991 and 1991)) also described in U.S. application Ser. No. 07/668,298 and Klein et al., (1991)) has shed new light on the identity and signal-transducing mechanism of the NGF receptor. Gp $140^{proto-trk}$ exhibited low affinity equilibrium binding, while expression of gp$75^{proto-trk}$ and gp $140^{proto-trk}$ in the same cell membrane regenerated a biphasic Scatchard profile similar to that seen in sensory neurons and PC12 cells. Thus, functional high affinity NGF receptors appear to require both gp $75^{NGFR}$ and the trk tyrosine kinase receptor (Kaplan et al., (1991); Hempstead et al., (1991)). Applicants have been led by their own prior work to examine whether the evolutionary cousin of trk, trkB, also serves as a receptor for neurotrophic factors (see also D. Soppets et al., *Cell* 65:985–903 (1991)).

The present invention relates, in part, to a complex comprising NGF ligand and the trk proto-oncogene receptor. It is demonstrated herein that direct binding of NGF to trk receptor leads to tyrosine phosphorylation and tyrosine kinase activity in response to NGF exposure in trk expressing cells. Knowledge of the trk physiological receptor and cognate NGF complex permits nerve growth and regeneration to be studied. Furthermore, the demonstration of NGF-trk receptor complexes offers methods for identifying related tyrosine kinase receptors providing additional neurotrophic-factor pairs. The invention further relates to a similar complex comprising the ligand NT-3 or BDNF complexed with trkB receptor, which complex can be isolated using the methods disclosed herein.

SUMMARY OF THE INVENTION

It is an object of the present invention to provide a complex comprising a nerve growth factor (NGF) ligand and trk-proto-oncogene protein receptor, related NGF-trk ligand/receptor complexes and methods of utilizing the complexes.

In one embodiment, the present invention relates to a complex of NGF and trk-proto-oncogene receptor protein wherein said complex is free of protein with which it is naturally associated.

In another embodiment, the present invention relates to a complex of NT-3 or BDNF and trkB-proto-oncogene receptor protein wherein said complex is free of protein with which it is naturally associated.

In another embodiment, the present invention relates to a complex comprising either NGF ligand and trk-protooncogene receptor protein or NT-3 or BDNF ligand and trkB-proto-oncogene receptor protein wherein one member of the complex is bound to a solid support.

In yet another embodiment, the present invention relates to a method of detecting the NGF:trk-proto-oncogene receptor complex, NT-3:trkB proto-oncogene receptor complex or BDNF:trkB proto-oncogene receptor complex in a sample. The method comprises contacting the sample with an antibody that binds specifically with NGF, NT-3, BDNF, trk- or trkb-proto-oncogene receptor protein of the complex. A positive immunological reaction is indicative of the presence of the complex in the sample.

In a further embodiment, the present invention relates to a method of diagnosing degenerative neuronal diseases in a patient suspected of having the disease. The method comprises contacting a sample of the diseased tissue with an antibody that binds with either the NGF:trk-proto-oncogene receptor protein complex or NT-3 or BDNF:trkB-proto-oncogene receptor protein complex. The contact is made under conditions such that complexation can occur and the presence of resulting complex is determined.

In yet another embodiment, the present invention relates to a method of diagnosing a tissue undergoing neuronal regeneration in a patient. The method comprises contacting a sample of the tissue with an antibody that binds to the NGF:trk-proto-oncogene receptor protein complex, NT-3:trkB-proto-oncogene receptor protein complex, or BDNF: trkB-proto-oncogene receptor protein complex under conditions such that complexation can occur and assaying for the presence of resulting complex.

In another embodiment, the present invention relates to a method of detecting NGF, NT-3 or BDNF neurotrophic factors in a sample. The method comprises contacting the sample with trk or trkB-proto-oncogene receptor protein under conditions such that binding of NGF, NT-3 or BDNF present in the sample to the receptor is effected and detecting the presence of bound NGF, NT-3 or BDNF. Likewise, the present invention relates to a method of detecting trk or trkB-proto-oncogene receptor protein in a sample using NGF, NT-3 or BDNF as the binding agent.

In further embodiments, the present invention relates to methods of detecting neurotrophic factor receptor/ligand complexes that are structurally and functionally related to trk and NGF comprising the methods described above for detecting trk:NGF, trkB:NT-3 and trkB:BDNF complexes.

Various other objects and advantages of the present invention will become apparent from the drawings and the following description of the invention.

The entire contents of all publications mentioned herein are incorporated by reference.

BRIEF DESCRIPTION OF THE DRAWINGS

FIG. 1A, gp140trk immunoprecipitated from PC12 cells or trk-expressing 3T3 cells labeled with $^{32}$P-orthophosphate. Immunoprecipitates were prepared with rabbit anti-trk antisera 43-4 (D. Martin-Zanca et al., *Mol Cell. Biol.* 9:24–33 (1989)) from lysates prepared from 3T3 cells expressing the rat trk gene (trk 3T3) (lane 1) or PC12 cells treated for 5 min with 100 ng/ml NGF at 37° C. (lanes 2 and 4) or mock treated (lane 3). The immunoprecipitate shown in lane 2 was prepared in the presence of the peptide used to generate the rabbit 43-4 trk antibody (Martin-Zanca et al., (1989)). Shown in FIG. 1B is the phosphoamino acid analysis of trk proteins phosphorylated in vitro in p140trk immunoprecipitates from NGF treated PC12 cells in vivo from NGF treated (+) or untreated (−) PC12 cells, or in vivo from trk 3T3 cells. The positions of phosphoserine (S), phosphothreonine (T), and phosphotyrosine (Y) are indicated. FIG. 1C, trk proteins from trk 3T3 cells phosphorylated in vivo or in vivo. In lanes 1–3, gp140trk immunoprecipitates were probed with P-tyr antibodies. In lanes 4–6, gp140trk proteins were phosphorylated in vitro in kinase assays. Cells were treated with suramin (lanes 2 and 5) or with 500 ng/ml NGF for 10 min following suramin treatment. The band migrating at 110 kDa is a glycosylation precursor of gp140$^{prototrk}$ (Martin-Zanca et al., (1989)). The band at the bottom of the figure is IgG. Molecular weight markers in kDa are indicated.

rtrk 3T3 cells were generated by $CaPO_4$ mediated transfection of a rat trk cDNA into NIH-3T3 cells. Rat trk cDNAs were obtained from an embryonic rat DRG cDNA library. The longest trk cDNA obtained (2.4 kbp) was missing approximately 150 bp of the coding region as compared to available mouse and human trk sequence. The missing bases plus minimal (~50 bp) 5' flanking non-coding sequences were replaced from mouse first coding exon sequences and the reconstructed gene was placed downstream of an MSV-LTR. PC12 cells or rtrk 3T3 cells (2×10$^7$) were labeled with $^{32}$P orthophosphate (1 mCi.ml in 4 ml) for 4 hr at 37° C. Cells were treated with NGF for the indicated times, washed, lysed in buffer containing 1% NP40, and the lysates immunoprecipitated with trk antibody 43-4 (D. R. Kaplan et al., *Cell* 61:125–133 (1990)) and electrophoresed on 7.5% SDS-PAGE gels as previously described (Kaplan et al., (1990)). For b, the phosphorylated trk bands were eluted from the gel and phosphoamino acid analysis performed as described (B. M. Sefton et al., *J. Cell* 24:165–174 (1981)). gp140trk protein from NGF treated PC12 cells was phosphorylated in vitro. For c, rtrk 3T3 cells were treated with 1 mM suramin in Dulbecco's Modified Eagle Medium (DMEM) for 2 h or mock treated. Following extensive washing of the cells with DMEM, NGF was added for the time indicated. Cells were lysed and the lysates were immunoprecipitated with trk antibody. Immunoprecipitates were either subjected to immunoblot analysis with the phosphotyrosine (Ptyr) monoclonal antibody 4G10 (Lanes 1–3), or were analyzed in kinase assays. (D. K. Morrison, et al. *Cell* 58:649–657 (1989) and Kaplan et al., (1990)). Similar amounts of trk protein were present in each lane.

Figure 2A:
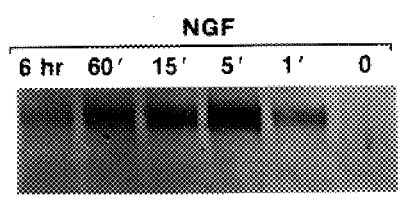
Figure 2B:
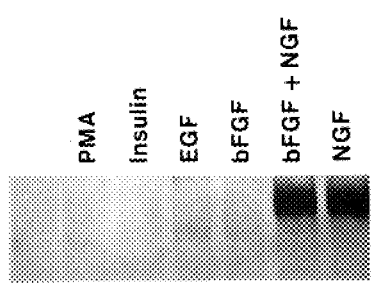
Figure 2C:
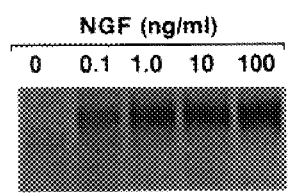

FIGS. 2A–C. Time course, growth factor specificity, and dose response of trk tyrosine phosphorylation in PC12 cells. A, Time course of trk tyrosine phosphorylation. Cells (2×10$^7$) were treated with 50 ng/ml NGF at 37° C. B, Effects of growth and differentiation factors on trk tyrosine phosphorylation. Cells were treated with 100 ng/ml NGF, 100 ng/ml basic fibroblast growth factor (FGF) (Boehringer Mannheim Biochemicals), 100 ng/ml epidermal growth factor (EGF) (Upstate Biotechnology, Inc.), 100 nM insulin (Sigma), or 1 $\mu$g/ml phorbal 12-myristate 12-acetate (PMA) (Sigma) for 15 min. at 37° C. C, dose response of trk tyrosine phosphorylation. Cells were treated for 30 min. at 37° C. with increasing concentrations of NGF. Shown are Western blot analysis with Ptyr antibodies of trk immunoprecipitates prepared with trk antibody 43-4.

Figure 3A:
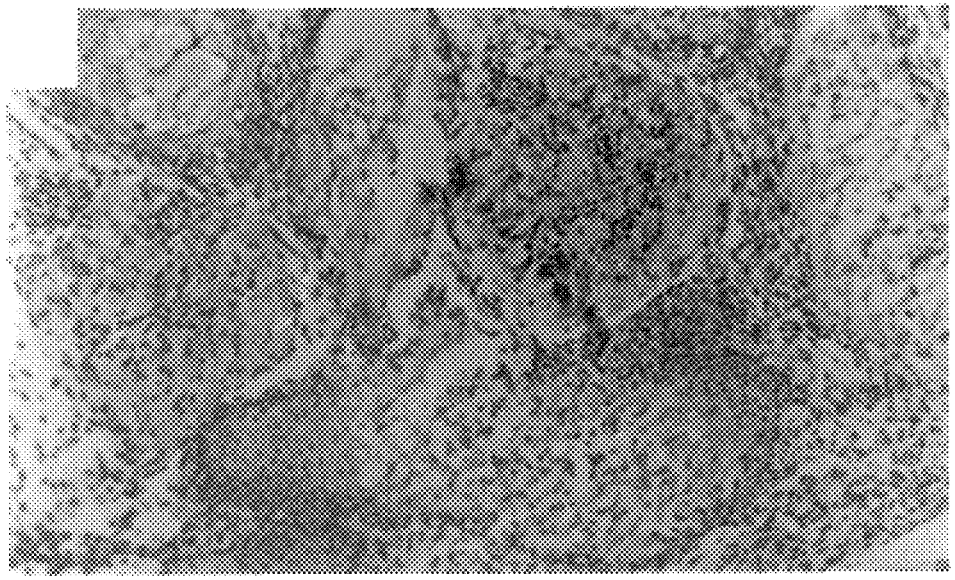
Figure 3B:
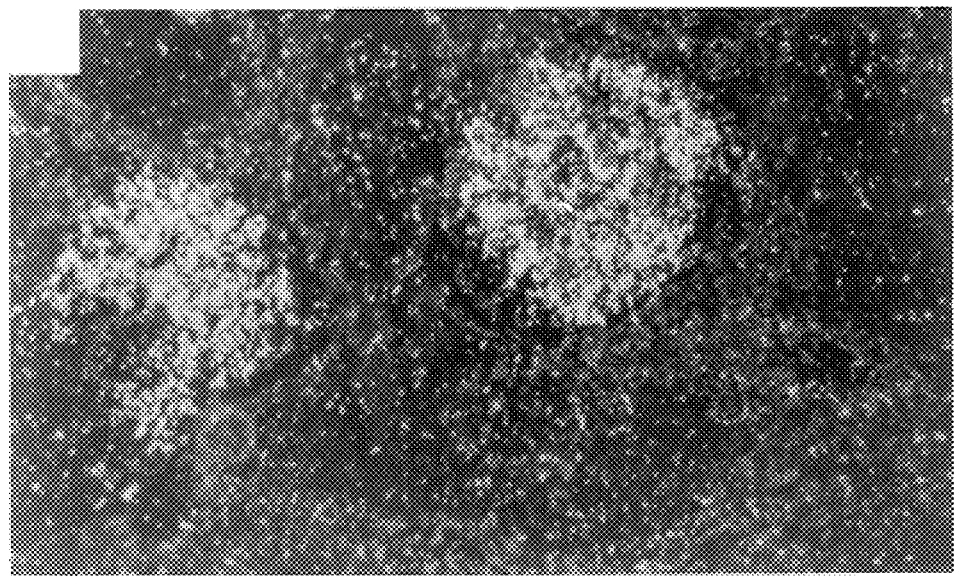

FIGS. 3A–B represent the trk expression in day 17 mouse embryo DRGs. FIG. 3A, Brightfield and FIG. 3B, darkfield optics of a sagittal section through the thoracic region of an E17 embryo. In situ protocols and probes have been described (Martin-Zanca et al., (1990)).

Figure 4A:
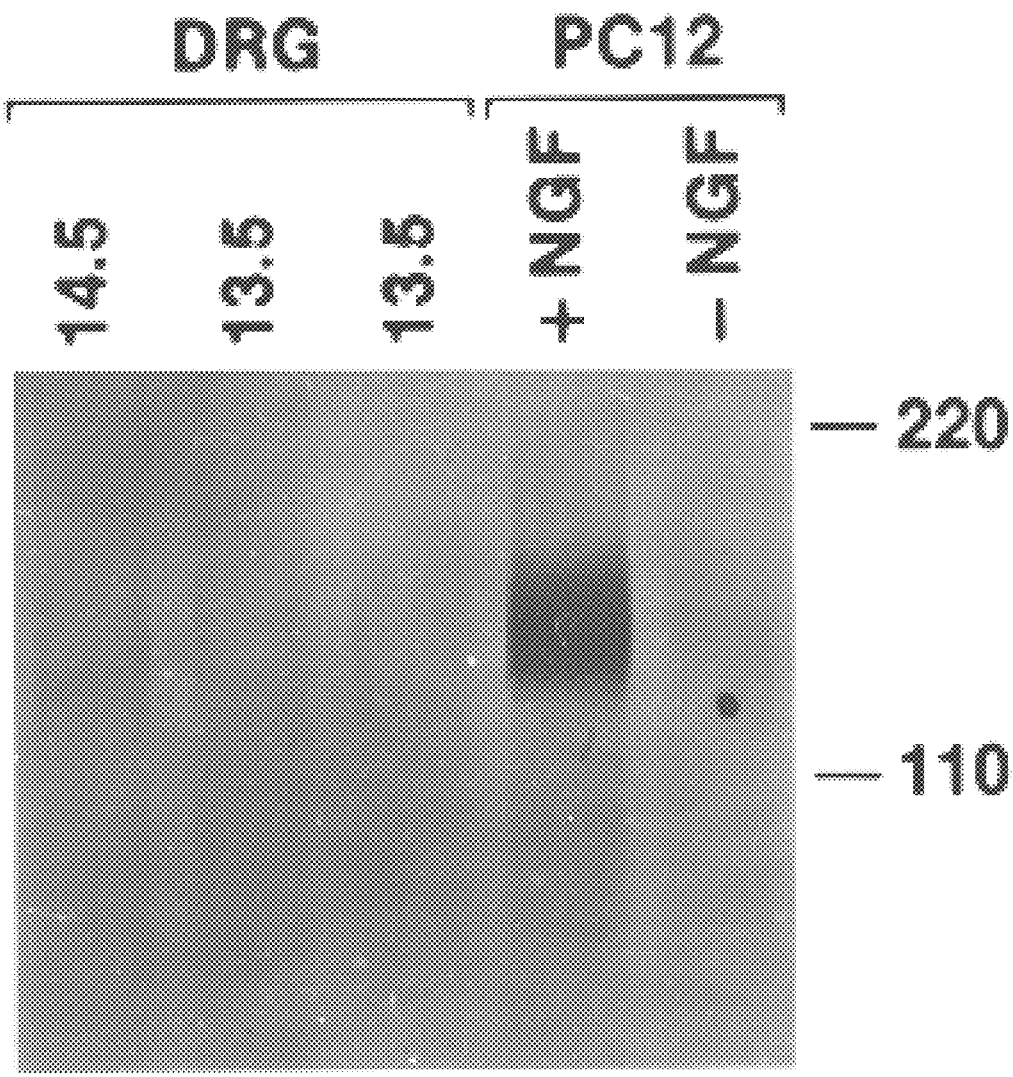
Figure 4B:
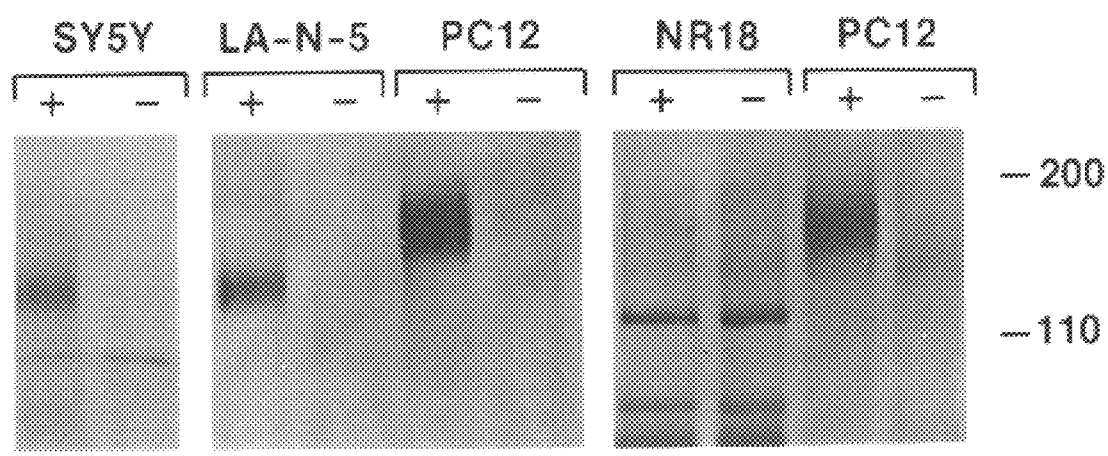

FIGS. 4A–B show NGF-dependent tyrosine phosphorylation of gp140trk in the human neuroblastoma cell lines LA-N-5, SY5Y, and dorsal root ganglia from mouse embryos. FIG. 4A, gp140trk was immunoprecipitated from untreated (−) or NGF treated (+) LA-N-5 cells (K. H. Sonnenfeld and D. N. Ishii, *J. Neurosci. Res.* 8:375–391 (1982)), SY5Y cells (K. H. Sonnenfeld and D. N. Ishii, (1982)), NR18 cells (M. A. Bothwell et al., *Cell* 21:857–866 (1980)), or PC12 cells. Immunoprecipitates were probed with P-tyr antibodies. The differences in trk protein mobilities are due to differences in glycosylation. FIG. 4B, Tyrosine phosphorylation of gp140trk in DRGs from 13.5 day or 14.5 day embryonic mice. DRGs were maintained in 100 ng/ml NGF for ≧10 min prior to lysis and immunoprecipitation with trk antibodies. trk immunoprecipitates were probed with P-tyr antibody. Tyrosine phosphorylated gp140trk from NGF-treated (+) PC12 cells or untreated (−) PC12 cells is shown for comparison. Samples were normalized for cell protein. Molecular weight markers in kDa are indicated.

Cell lines were treated with 100 ng/ml NGF for 5 min and gp140trk immunoprecipitated as in FIG. 1. DRGs were prepared by dissection for 13.5 or 14.5 day mouse embryos. 100 DRG's were treated with NGF, washed, and subjected to Dounce homogenization in 1% NP40 lysis buffer. Lysates were immunoprecipitated with trk antibody and the trk proteins were analyzed by antiphosphotyrosine immunoblots.

Figure 5:
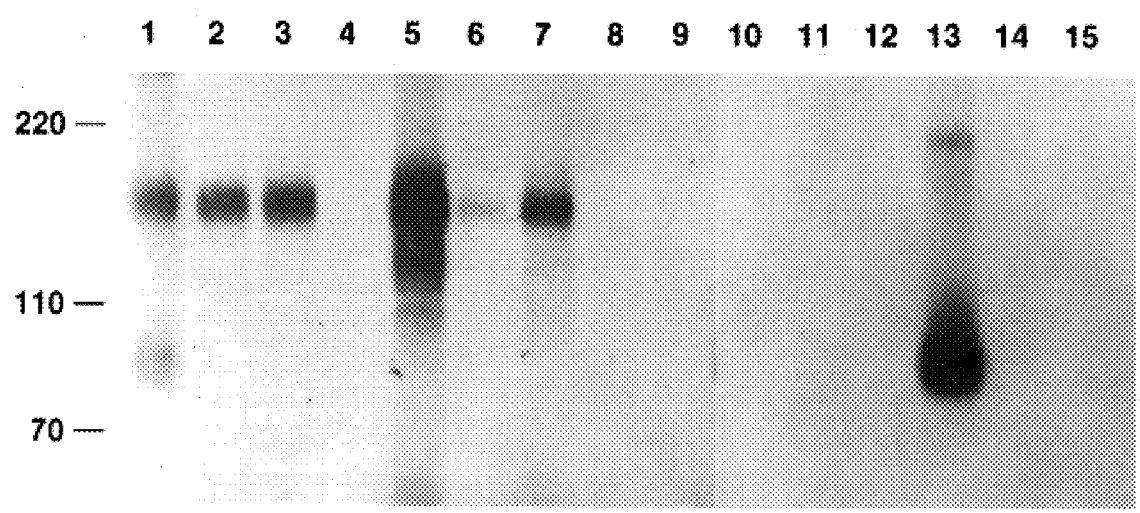

FIG. 5 depicts the affinity crosslinking of NGF to gp140trk on PC12 cells and rtrk 3T3 cells. trk receptors were labeled by cross-linking of $^{125}$I-NGF to cultured cells using HSAB. The cell lines analyzed were PC12 cells (lanes 1–4), rtrk 3T3 cells (lanes 5–9), NIH-3T3 cells (lanes 10–11) and A875 human myeloma cells (lanes 13–15). Lysates from cells were immunoprecipitated with anti-NGF (lanes 1, 5, 9–14), gp140trk antibody 7-4 which is another trk antibody generated in bacteria against the gp70trk oncogene (7-4), (Martin-Zanca et al., (1989)) (lanes 2 and 6), or gp140trk antibody 43-4 in the absence (lanes 2, 7 and 15) or presence (lanes 4 and 8) of 10 μg/ml competing trk peptide. Crosslinking was performed in the presence of excess unlabeled NGF (5 μm) in lanes 9, 11, and 14. The antibody 7-4 immunoprecipitates 3–5 fold less gp140 trk than does antibody 43-4. Molecular weight markers in kDa are indicated.

$^{125}$I-NGF was prepared by lactoperoxidase treatment to specific activities of 2500–3500 cpm/fmole. Crosslinking of gp140trk to $^{125}$I-NGF was performed as described by B. L. Hempstead et al. (*Science* 243:373–375 (1989), Hempstead et al. (1990)). Cells (2×10$^6$/ml) were incubated with 0.5 nM $^{125}$I-NGF for 2 hr at 4° C. HSAB (50 μM) was added and the reaction exposed to long ultraviolet wavelength for 10 min. After washing in 50 mM lysine in phosphate buffered saline, cells were lysed in buffer containing 1% NP40 and the lysates immunoprecipitated and analyzed on 7.5% SDS-PAGE as described (Kaplan et al., (1990)).

FIGS. 6A–B demonstrate the equilibrium binding analysis of trk receptors in cell membranes prepared from rtrk 3T3 cells. Binding of $^{125}$I-NGF was analyzed in crude membrane preparations by filter binding as described (Hempstead, et al., (1989)). Reactions were carried out in triplicate in the presence or absence of excess unlabeled NGF with 10 g of membrane protein for 1 hr. at 30° C. and filtered under vacuum through Millipore HVPL filters. Over 80% of specific binding was detected after subtracting values obtained in the presence of unlabeled NGF. FIG. 6A) Saturation binding curve; and FIG. 6B) data in (FIG. 6A) plotted according to Scatchard. Only binding values above 50% specific binding were used. The LIGAND program was used to determine $K_d$.

Figure 7:
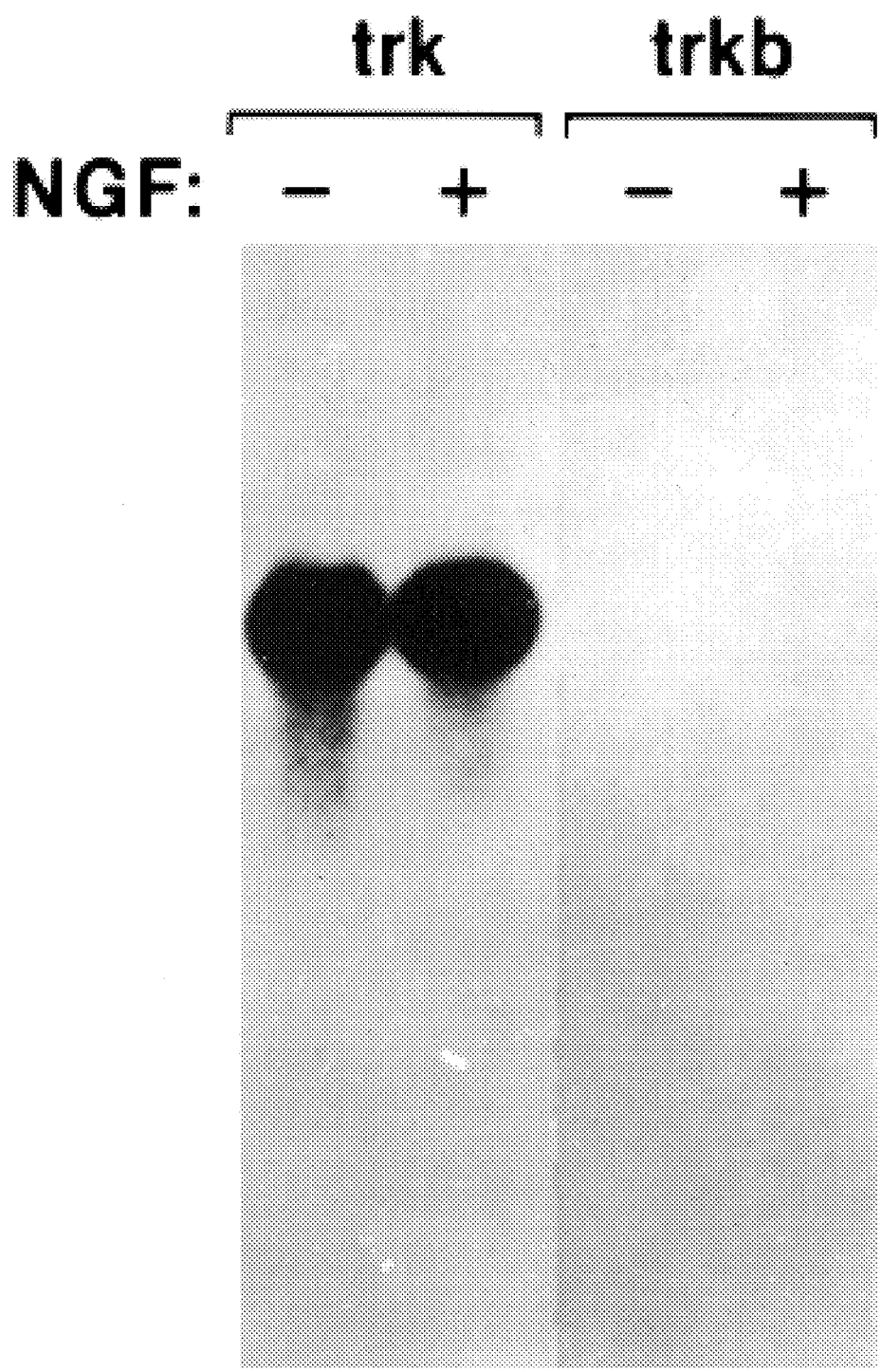

FIG. 7 shows the Northern transfer analysis of trk and trkB transcripts in NGF treated (+) or untreated (−) PC12 cells. RNA preparation and Northern transfer analysis was performed as described (Martin-Zanca et al., (1990a)). Cells were treated with 50 ng/ml NGF(+) (Boehringer Mannheim Biochemicals) and were harvested 48 hr later after differentiation had occurred. 20 μg of total RNA was loaded per lane, and the filter was hybridized with a trk (Martin-Zanca et al., (1990)) or trkB (Klein et al., (1990a)) specific probe.

Figure 8:
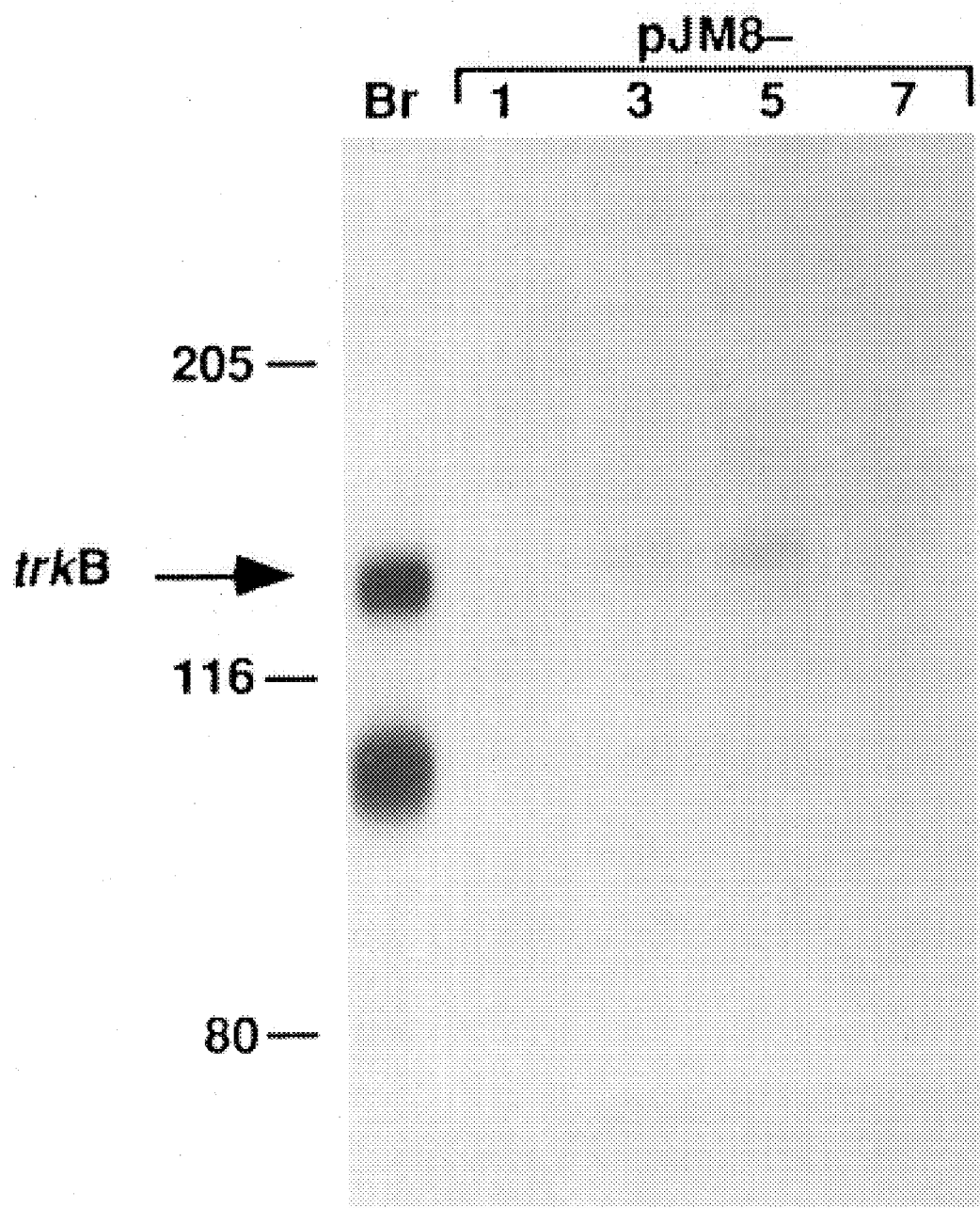

FIG. 8 shows the identification of NIH 3T3 cell lines expressing gp 145$^{trkB}$. gp 145$^{trkB}$ expression in NIH 3T3 cell lines was detected by Western transfer analysis of WGA-Sepharose precipitated glycoproteins from independent G418-resistant colonies using gp145$^{trkB}$ antiserum 442. Cell lines pJM8-1, -3, -5, and -7 and mouse brain extract (Br) are indicated. Molecular weight markers with apparent sizes in kDa and gp145$^{trkB}$ are indicated.

Figure 9:
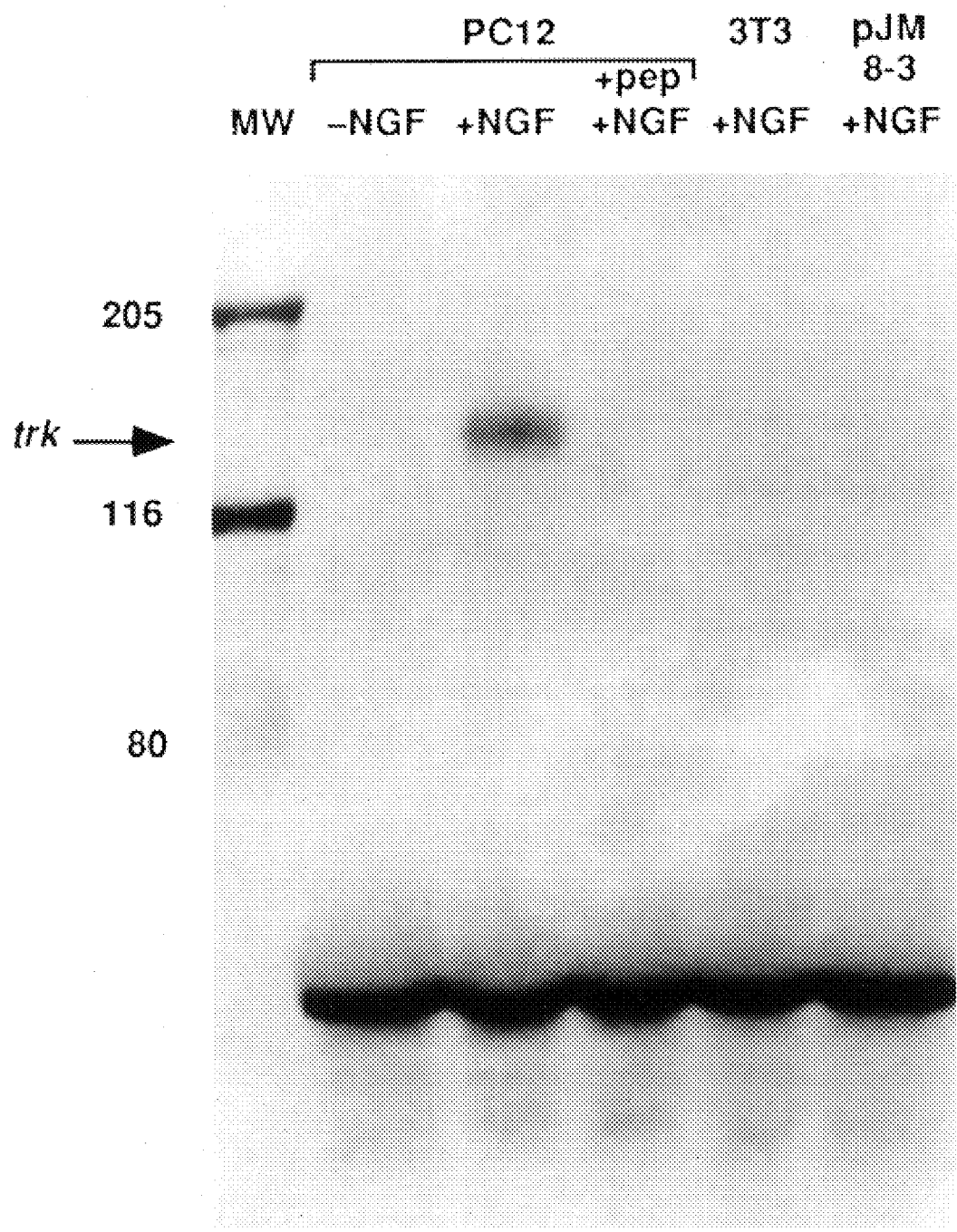

FIG. 9 shows that NGF treatment does not stimulate tyrosine phosphorylation of gp145$^{trkB}$. Tyrosine phosphorylation of immunoprecipitated gp145$^{trkB}$ following NGF treatment was monitored by Western transfer analysis as described in the Examples. The blotted filter contains the following, in order: untreated PC12 cells, NGF-treated PC12 cells, NGF-treated PC12 cells immunoprecipitated in the presence of 10 μg/ml competing peptide (+pep), NGF-treated NIH 3T3 cells, and NGF-treated trkB-expressing cell line pJM8-3. Molecular weight markers with apparent sizes in kDa and gp140$^{proto-trk}$ are indicated.

Figure 10:
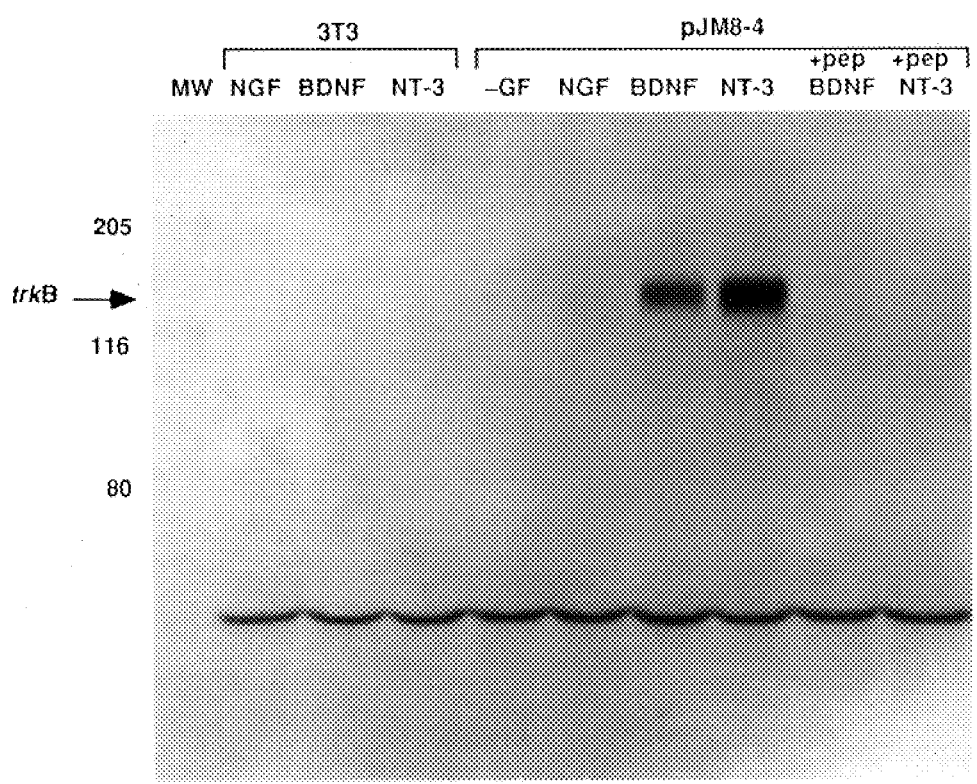

FIG. 10 depicts gp145$^{trkB}$ phosphorylation of tyrosine in response to BDNF or NT-3. Tyrosine phosphorylation of immunoprecipitated gp145$^{trkB}$ after a 5 min treatment of cells with 100 ng/ml NGF, BDNF, or NT-3 was determined by α-Ptyr Western transfer analysis as described in the Examples. NIH 3T3 (3T3) or gp145$^{trkB}$-expressing NIH 3T3 cells (pJM8-4) were used, as indicated. The lanes contain the following: NGF-, BDNF-, or NT-3-treated NIH 3T3 cells, or gp145$^{trkB}$-expressing cell line pJM8-4 without growth factor (−GF) or with NGF, BDNF, or NT-3 treatment. The treated cells were immunoprecipitated in either the presence or absence of 10 μg/ml competing peptide (+pep), as indicated. Molecular weight markers with apparent sizes in kd and gp145$^{trkB}$ protein are indicated.

Figure 11:
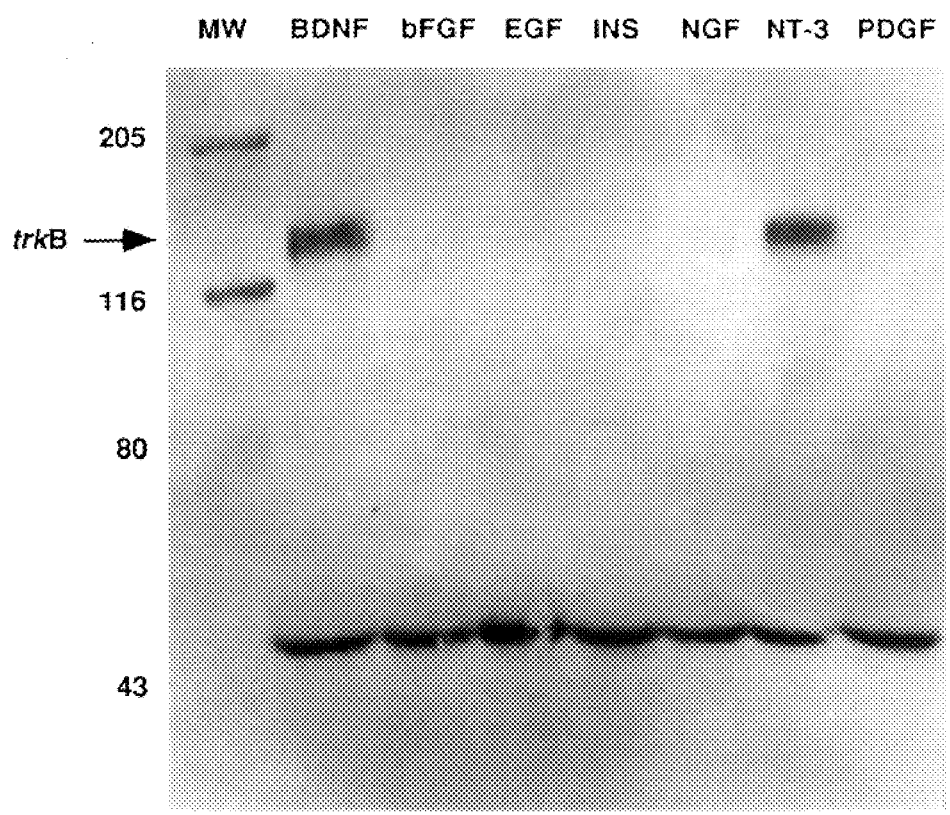

FIG. 11 shows growth factor specificity of gp145$^{trkB}$ tyrosine phosphorylation. Tyrosine phosphorylation of immunoprecipitated gp145$^{trkB}$ is shown after treatment with growth factors that activate tyrosine kinases in fibroblasts as well as NGF in gp145$^{trkB}$-expressing cell line pJM8-3. Growth factor stimulation and α-Ptyr Western transfer analysis were performed as described in the Examples. The lanes contain cells treated for 5 min with BDNF, bFGF, EGF, insulin (INS), NGF, NT-3, or PDGF. Molecular weight markers with apparent sizes in kDa and gp145$^{trkB}$ protein are indicated.

Figure 12:
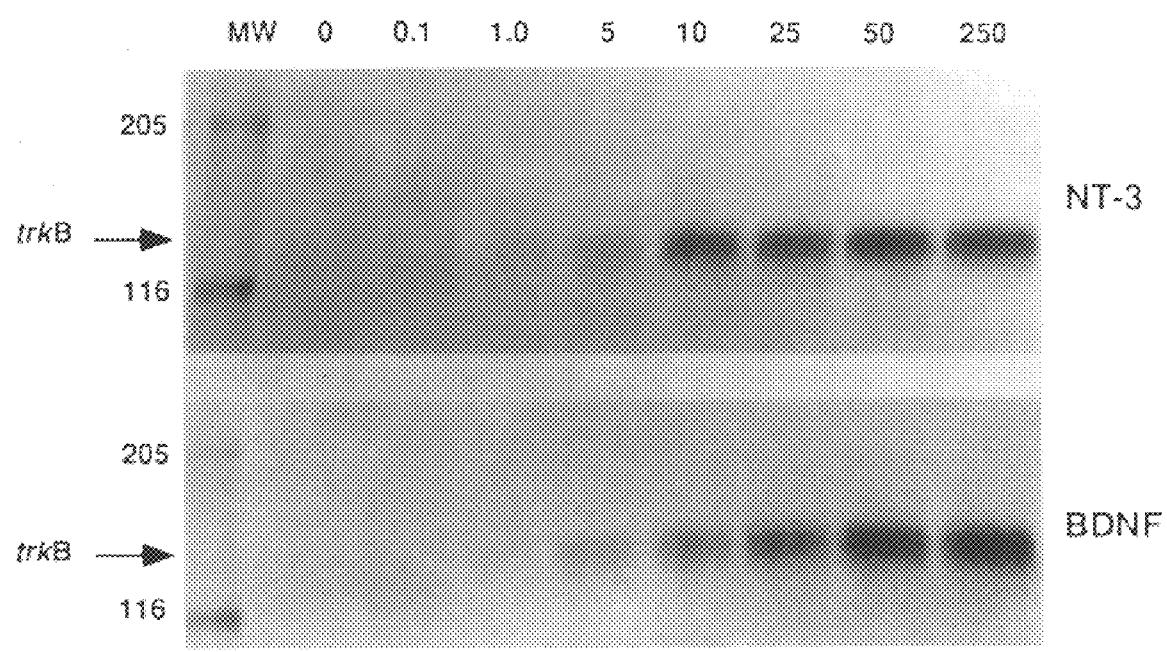

FIG. 12 shows gp145$^{trkB}$ tyrosine phosphorylation as a function of BDNF or NT-3 concentration. Dose-response of gp145$^{trkB}$ phosphorylation to increasing concentrations of NT-3 (upper panel) or BDNF (lower panel). gp145$^{trkB}$ tyrosine phosphorylation in trkB-expressing cell line pJM8-3 was detected by immunoprecipitation and α-ptyr Western transfer analysis as described in the Examples. The lanes contain the following: no added NT-3 or BDNF (0) or 0.1, 1, 5, 10, 25, 50, or 250 ng/ml NT-3 or BDNF, as specified. Molecular weight markers with apparent sizes in kDa and gp145$^{trkB}$ protein are indicated.

Figure 13:
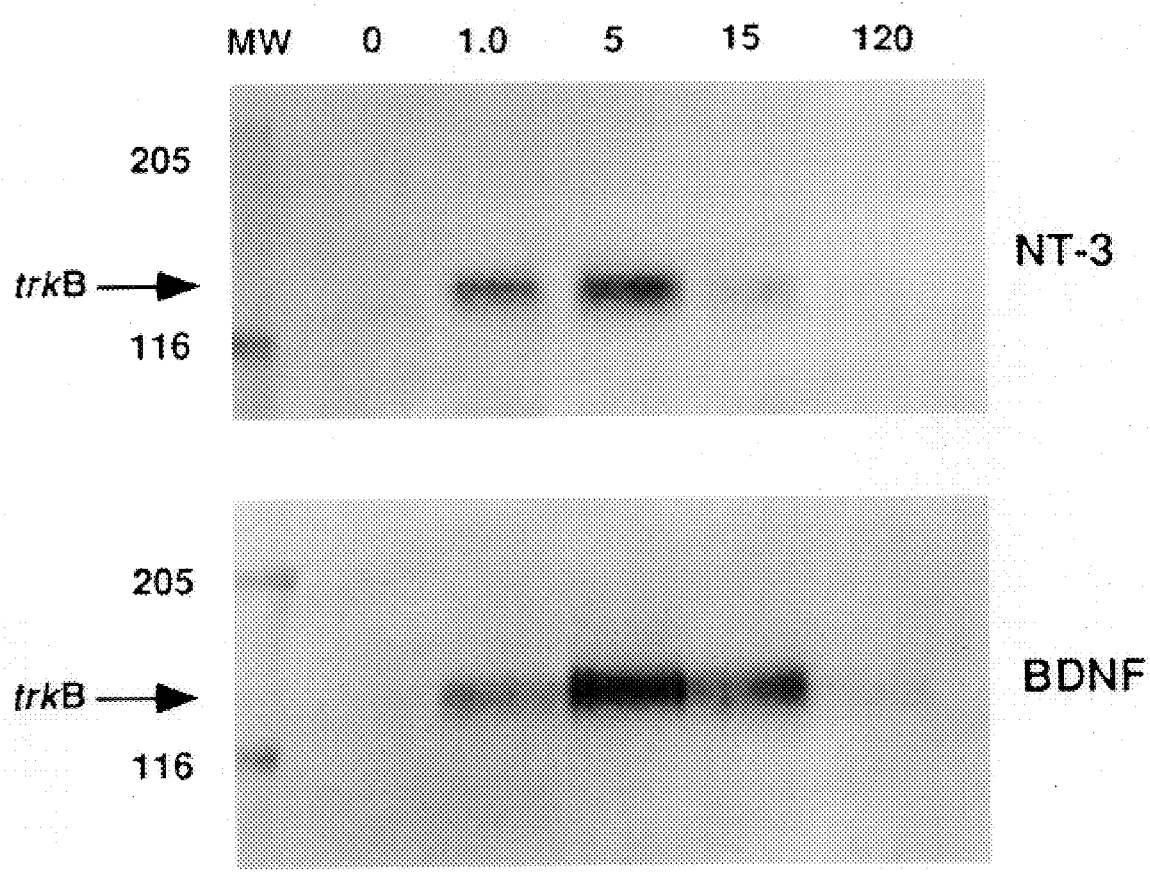

FIG. 13 shows that gp 145$^{trkB}$ is rapidly phosphorylated on tyrosine upon exposure to NT-3 or BNDF. Time course of gp 145$^{trkB}$ phosphorylation in PJM8-3 cells after treatment with 100 ng/ml NT-3 (upper panel) or BDNF (lower panel) for 1, 5, 15, or 120 min, as indicated. gp 145$^{trkB}$ tyrosine phosphorylation was determined by immunoprecipitation and α-ptyr Western blot analysis as described in the Examples. The lanes contain the following: gp145$^{trkB}$ prior to growth factor addition (0) or gp 145 1, 5, 15, or 120 min after exposure to NT-3 or BDNF. Molecular weight markers with apparent sizes in kDa and gp 145$^{trkB}$ protein are indicated.

DETAILED DESCRIPTION OF THE INVENTION

The present invention relates to a complex comprising nerve growth factor (NGF) and trk-proto-oncogene protein and a complex comprising either NT-3 or BDNF factor and trkB-proto-oncogene protein. The present invention further relates to methods of utilizing the complexes.

The present invention relates to a complex formed by the interaction of NGF with trk-proto-oncogene protein that is free of proteins with which it is naturally associated. The trk-proto-oncogene product is a 140 kDa glycoprotein tyrosine kinase and a component of the high affinity NGF receptor. The present invention further relates to a complex formed by the interaction of either NT-3 or BDNF with trk-b-proto-oncogene receptor protein that is free of other proteins to which it is naturally associated. The trkB proto-oncogene product is a 145 kDa glycoprotein tyrosine kinase and a component of the high affinity NT-3 and BDNF receptor. The invention also relates to detection and quantitation methods that can be used to identify, in a sample, NGF, NT-3 or BDNF (ligands) and trk or trkB-proto-oncogene protein receptors as they are associated with each other in ligand-receptor complexes.

Neurons of the central and peripheral nervous system are dependent on NGF for their continued survival. To date, NGF-dependent neurons that have been identified are sensory neural crest-derived (trigeminal, superior, jugular and dorsal rout ganglia neurons), sympathetic neurons and cholinergic neurons of the basal, media septal and diagonal septal band nuclei of the brain. This last neuronal type is found to be degenerative in Alzheimer's and Huntington's disease.

One skilled in the art will appreciate that the knowledge and understanding of NGF-mediated responses as occurring via a complex with the trk tyrosine kinase has broad implications for the study of nerve survival, regeneration and accurate diagnosis and potential therapy for neurodegeneratives diseases that affect NGF-dependent neurons.

Since NGF-dependent neurons respond via the NGF-trk proto-oncogene tyrosine kinase complex, the methods described herein provide a means for identifying other neuronal types other than those described above which can lead to the identification of neuronal disorders. In this regard, Applicants have identified trk expression (and therefore NGF-responsive neurons) in the trigeminal mesencephalic nucleus. These neurons mediate many important sensory functions throughout the brain and may be affected in as yet unidentified neuronal disorders.

The methods of the present invention can aid in the understanding of the role of the interaction between NGF and its receptor, the trk-proto-oncogene product as a transducer of NGF signals. Prior studies of tyrosine kinases in other biological systems (i.e., oncogenesis and cell growth) indicate that biochemical cascades exist within the cell that are the signal transducing pathways to the nucleus. Thus NGF binding to trk initiates a signal cascade inside the cell that is amenable to identification, study, and ultimately, to manipulation, utilizing skills and methodologies known in the art.

Using standard methodologies well known in the art (and described herein), a biological sample can be extracted, for example, with a non-ionic detergent and incubated with labeled NGF (for example, NGF labeled with $^{125}$I or fluorescein) in the presence or absence of unlabeled NGF. The resulting complex can be separated from the uncomplexed (or unbound) labeled material. Separation can be effected by immuno- precipitating the complex with a specific polyclonal antibody (for example, the 43-4 or 4.7 rabbit anti-trk antisera) and in parallel, a monoclonal phosphotyrosine antibody, such as Ptyr 4G10, that recognizes the trk-proto-oncogene receptor protein or the NGF-trk proto oncogene receptor complex. The overall signal resulting from the presence of label associated with the complex is compared with the signal from a mock sample. The mock sample is prepared using purified trk-proto-oncogene receptor protein in a known quantity treated the same way as the biological sample. Alternatively, the complex can be separated from uncomplexed material by precipitating with polyethylene glycol. In either methodology, the amount of label that is immunoprecipitated or precipitated is directly related to the amount of complex in the biological sample.

The invention also includes a method of detecting and quantitating NGF in a biological sample using labeled trk-proto-oncogene receptor as a probe. The method can be carried out as a reciprocal binding assay following the methodology described above except substituting as antibody, one that specifically recognizes NGF or the NGF-trk-proto-oncogene receptor complex. Antibodies against NGF are well known in the art.

The present invention also relates to further methods of detecting and quantitating NGF-trk-proto-oncogene protein receptor complexes in a sample. In one embodiment, complexes are detected and quantitated using antibodies directed against NGF, trk-proto-oncogene receptor protein or the NGF-receptor complex. Antibodies can be either polyclonal or monoclonal; examples of both are described above and below in the Examples. A sample can be extracted with non-ionic detergent and incubated with labeled NGF or trk-proto-oncogene receptor protein. After incubation, the sample is covalently cross-linked with a lipophilic photoaffinity cross-linking agent for example, HSAB. Chemical crosslinking agents, such as disuccinimidil suberate (DSS) can be used in this procedure. The sample can be immunoprecipitated with specific antibody or precipitated with polyethylene glycol. Quantitation requires chromatographic separation by, for example, gel electrophoresis, followed by autoradiography.

The present invention also relates to diagnostic methodologies using the methods described above. The disorders which are diagnosed by the methods of the present invention include, for example, neurodegenerative diseases that affect NGF-dependent neurons such as Alzheimer's and Huntington's diseases. The present diagnostic methods can also be used to measure neuronal disorders in tissue derived from neuronal cell types described previously, which may lead to diagnosis of as yet unidentified neuronal disorders.

The present invention further relates to methods of detecting other trk related receptor and NGF related neurotrophic factor complexes using methods similar to those utilized above for detecting the trk/NGF complex. The trk gene is a member of a structurally related gene family of which at present at least three members have been identified (trk, trkB, and trkc). Likewise a growing number of neurotrophic factors are emerging on the basis of similar structure and function to NGF such as BDNF and NT-3, for example. It is very likely that methods used to identify the trk/NGF complex will lead to parallel discoveries with the additional trk and NGF-related genes. Identification and characterization of these trk-related/NGF-related complexes (ie. trkB/BDNF and trkB/NT-3) can be carried out in a manner described generally above and in greater detail in the Examples that follow. Any implications at the practical or therapeutic levels will apply to these neurotrophic factors. The knowledge of trk-related/NGF-related complexes, for example, trk/BDNF and trkB/NT-3, will provide insight into the survival capacities of a different subset of nerve cells to those dependant on NGF. Similar assays and strategies previously described to those conceived or devised for detecting the trk/NGF complex apply to the detection of the related complex, for example, use of phosphotyrosine and trkB antibodies for immunoprecipitating trk-related/NGF-related complexes.

The present invention further relates to complexes formed by the interaction of NT-3 or BDNF with trkB proto-oncogene receptor that is free of protein with which it is naturally associated. As discussed above, NT-3 and BDNF shares strong structural homology to NGF as determined by molecular cloning in addition to sharing the biological characteristics of neurotrophins. Direct evidence that trkB is a receptor for NT-3 and BDNF was determined by measuring the phosphorylation state of the trkB receptor in cells after NT-3 or BDNF was added to the medium. The methods utilized to detect and quantitate the NT-3-trkB or BDNF-trkB proto-oncogene receptor complex are analogous to those performed with trk-expressing cells and NGF described herein. The only difference in the method for detecting trkB-NT-3 and trkB-BDNF complexes in trkB expressing cells is that the antibodies are directed against different neurotrophic factors, i.e., NT-3, BDNF, a trk-related gene product, i.e., trkB-proto-oncogene receptor and the complexes they form, i.e., NT-3-trkB and BDNF-trkB-receptor complex. Similarly, the method for detecting and quantitating trkB receptor, NT-3 or BDNF in a biological sample is performed following the methodology described herein except for the substitution of NT-3 or BDNF antibodies or trkB-proto-oncogene receptor antibodies where applicable. Antibodies against NT-3 and BDNF are well known in the art.

Moreover, trk and trkB receptor antibodies can be used interchangeably in the methods described above with knowledge of the specific tissue which expresses either trk or trkB receptor.

The present invention further relates to therapeutic methodologies that enhance NGF, NT-3 or BDNF mediated nerve regeneration or survival, and to pharmaceutical compositions suitable for use in same. Such methodologies depend on the use of specific trk or trkB related member antibodies and phosphotyrosine antibodies to assay for the effectiveness of the procedure.

Of importance in the area of therapeutics is the development of drugs that either enhance or inhibit tyrosine phosphorylation Since trk or trkB related members mediate signalling via phosphorylation on tyrosine of messenger molecules, its signalling could be altered as required in cells. Potential drugs can be added to trkB (or trkB related member) expressing tissue culture cells, together with or in the absence of NGF, and the state of trk or trkB-related member activation (as measured by tyrosine phosphorylation) can be assessed.

The effect of these drugs can be monitored with antibodies that recognize trk or trkB-related members and/or phosphorylated tyrosines. Thus, development of useful therapies in this area will depend on the ability to identify the activation state of trk or trk-related members and/or any of its downstream substrates. Animal models (for example, rat or mouse) can be used in which specific nerve connections are disrupted, the promising pharmaceuticals administered, and finally analysis of the sacrificed animals performed to assess the regeneration of nerves using trk/NGF or trk-related member/NGF-related ligand antibody assays as described.

The present invention also relates to other therapeutic methods for designing pharmaceuticals that enhance the stimulation of degenerative nerves in diseases such as Alzheimer's and Huntington's.

trk and low affinity NGF receptor 75/KNGF-R are required together for high affinity response to NGF. Methods can be devised that would enhance detection of NGF using the high affinity complex. Knowledge of the existence of a trk/NGF complex can be expected to lead to the development of modified NGF molecules that hyperstimulate trk activation. These NGF derivatives might be of importance in the stimulation of degenerating nerves stemming from diseases, for example, Alzheimer's and Huntington's, or from injury.

Many substrates of tyrosine kinases have been identified. Identification of trk-specific substrates may lead to discovery of an intermediate molecule in the NGF pathway that can be manipulated pharmacologically to enhance or inhibit NGF-mediated signals.

Certain aspects of the present invention are described in greater detail in the following non-limiting Examples.

EXAMPLES

The following materials and procedures are referred to in the Examples that follow.

Materials

WGA-Sepharose 6B and protein A-Sepharose 4B were from Pharmacia (Piscataway, N.J.). Alkaline phosphatase-conjugated anti-mouse and anti-rabbit antibodies, BCIP, and nitro blue tetrazolium were from Promega Biotec (Madison, Wis.). Monoclonal antibody 4G10 supernatant was kindly provided by Dr. D. Morrison. Peptides and antisera were generated at NCI-FCRDC. Dulbecco's modified Eagle's medium (DMEM), Leibovitz L-15 medium, trypsin, calf serum, and horse serum were from Gibco-BRL (Grand Island, N.Y.). HPLC-purified NGF, NT-3, and BDNF were supplied by Genentech (South San Francisco, Calif.). Prestained molecular weight markers were purchased from Bio-Rad (Richmond, Calif.). Protease inhibitors and ortho-vanadate were from Sigma (St. Louis, Mo.).

Antisera and Antibodies

Rabbit polyclonal antisera were raised against KLH-conjugated synthetic peptides corresponding to amino acids 45–60 (peptide and antiserum 442) and 807–821 (peptide and antiserum 443) of mouse trkB (E. Escandon and M. V. Chao *Dev. Biol.* 142:293–300 (1990)). Antiserum 442 detects gp $145^{trkB}$ at 1:2000 dilutions by Western transfer analysis and does not recognize gp $140^{proto-trk}$ at dilutions of 1:500 by Western transfer analysis. Antiserum 443 was used for immunoprecipitations of both gp $140^{proto-trk}$ and gp$145^{trkB}$. α-Ptyr analysis and immunoprecipitations were performed with monoclonal antibody 4G10 as described (D. K. Morrison et al., *Mol. Cell. Biol.* 8:176–185 (1988)).

Construction of trkB-Expressing Cell Lines

A 4.8 kb cDNA encompassing the coding domain of rat trkB (Middlemas et al., (1991)) was cloned into the pMEX plasmid (pJM8) downstream of the MSV promoter. NIH 3T3 cells were cotransfected with the pJM8 plasmid and a plasmid containing the neomycin phosphotransferase gene (L. F. Parada et al., Nature 312:649–651 (1984)), and G418-resistant colonies were selected. PC12 cells (Greene and Tischler, 1976) were grown in DMEM with 10% horse serum and 5% fetal calf serum. NIH 3T3 cells and the derivative cells lines were maintained in DMEM medium containing 10% calf serum. All cells were maintained in a humidified incubator at 37° C. in 5% $CO_2$.

Identification of $gp145^{trkB}$-Expressing Cell Lines

Expression of $gp 145^{trkB}$ was detected in G418-resistant clonal cell lines by WGA-Sepharose precipitation and Western transfer analysis as previously described (Kaplan et al., (1991); Morrison et al., (1989)). Approximately $2 \times 10^6$ cells were lysed in 1 ml of ice-cold lysis buffer (1% NP-40, 20 mM Tris [pH 8.0], 150 mM CaCl, 1 mM PMSF, 1 mM orthovanadate, 5 μg of pepstatin A, and 10 ng of leupeptin) at 4° C. for 20 min. The lysates were cleared by centrifugation at 4° C. for 10 min at 12,000×g. Glycoproteins were absorbed by adding 75 μl of a 1:1 suspension of WGA-Sepharose in 1% NP-40, 20 mM Tris [pH 8.0], 150 mM NaCl (NP-40 buffer) to each tube, and the suspension was gently mixed at 4° C. for 2 hr. The WGA-Sepharose was pelleted and the beads washed three times with 1.5 ml of NP-40 buffer. Protein was released from the beads by heating to 95° C. in 2% SDS. 100 mM Tris (pH 6.8), 100 mM DTT, 10% glycerol, and 0.25% bromophenol blue (sample buffer). The protein samples were resolved on a 7.5% polyacrylamide gel (U. K. Laemmli, Nature 227:680–685 (1970)). Electrophoretic transfer to 0.2 μm nitrocellulose was performed at 0.4 A for 4 hr in 25 mM Tris-HCl, 92 mM glycine, 20% methanol, and 0.0125% SDS. The filters were blocked with 2% BSA in 20 mM Tris (pH 7.5), 150 mM NaCl for 1 hr at room temperature and probed with a 1:2000 dilution of rabbit polyclonal antiserum 442 in 20 mM Tris (pH 7.5), 150 mM NaCl, 0.05% Tween 20, 0.02% sodium azide (TBST). After washing with TBST, an alkaline phosphatase-conjugated anti-rabbit antibody was applied for 60 min at room temperature at 1:7000 dilution. The blots were washed and then developed in 100 mM Tris (pH 9.5), 100 mM NaCl, 5 mM $MgCl_2$, with 0.03% BCIP and 0.06% nitro blue tetrazolium. $gp145^{trkB}$ and $gp95^{trkB}$ were precipitated from two adult mouse brains. The brains were homogenized in ice-cold lysis buffer and then cleared by centrifugation at 10,000×g for 10 min at 4° C. Glycoproteins were precipitated with a 500 μl suspension of WGA-Sepharose as previously described. The WGA-precipitated proteins were heated in sample buffer and aliquots stored at −20° C. for Western analysis.

Growth and Neurotrophic Factor Stimulation of Cell Lines

Approximately $10^7$ cells were treated at 37° C. for 5 min with 100 ng/ml growth factors or at the concentrations and lengths of time noted in the text. NP-40 plate lysis and $gp145^{trkB}$ immunoprecipitation with anti-serum 443 were performed as previously described (Kaplan et al., (1990), (1991)). The phosphotyrosine content was analyzed by Western transfer using monoclonal antibody 4G10 as previously described (Morrison et al., (1989)).

Example 1

Tyrosine Phosphorylation of $gp140^{prototrk}$ in Response to NGF

Figure 1A:
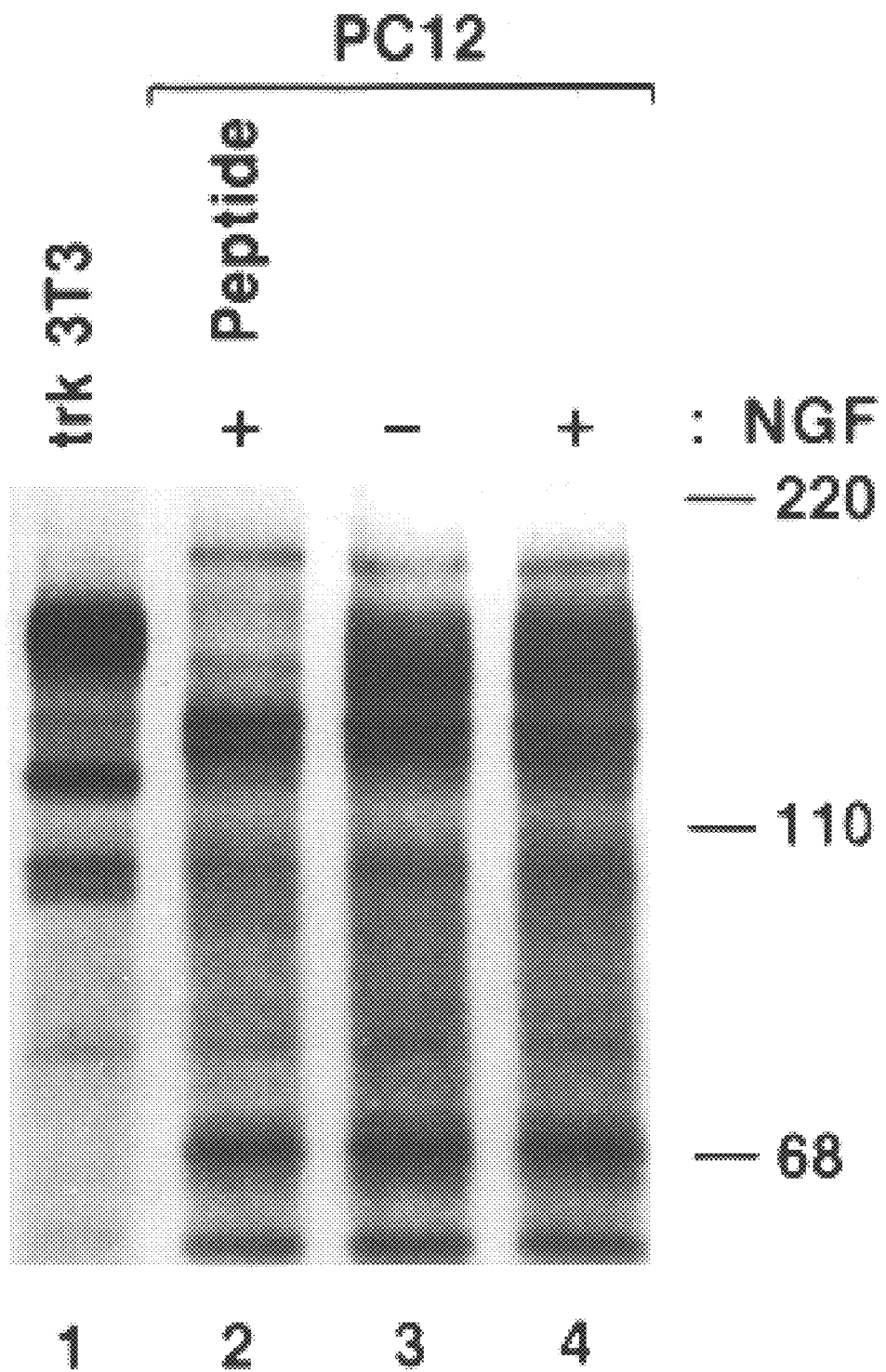
FIGS. 1A–C show the tyrosine phosphorylation of gp140trk in PC12 cells and trk-expressing NIH-3T3 cells treated with NGF.
Figure 1B:
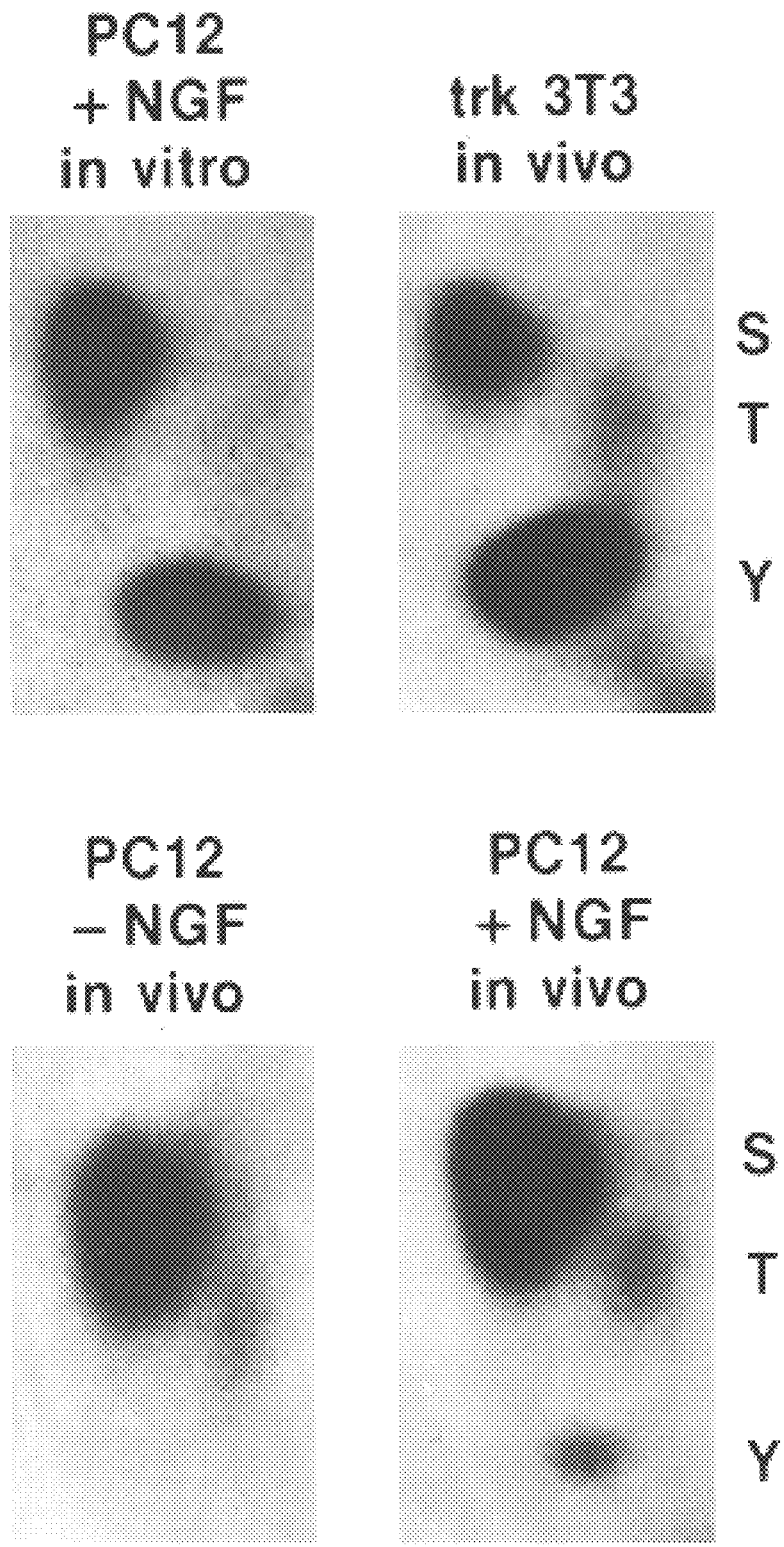
Figure 1C:
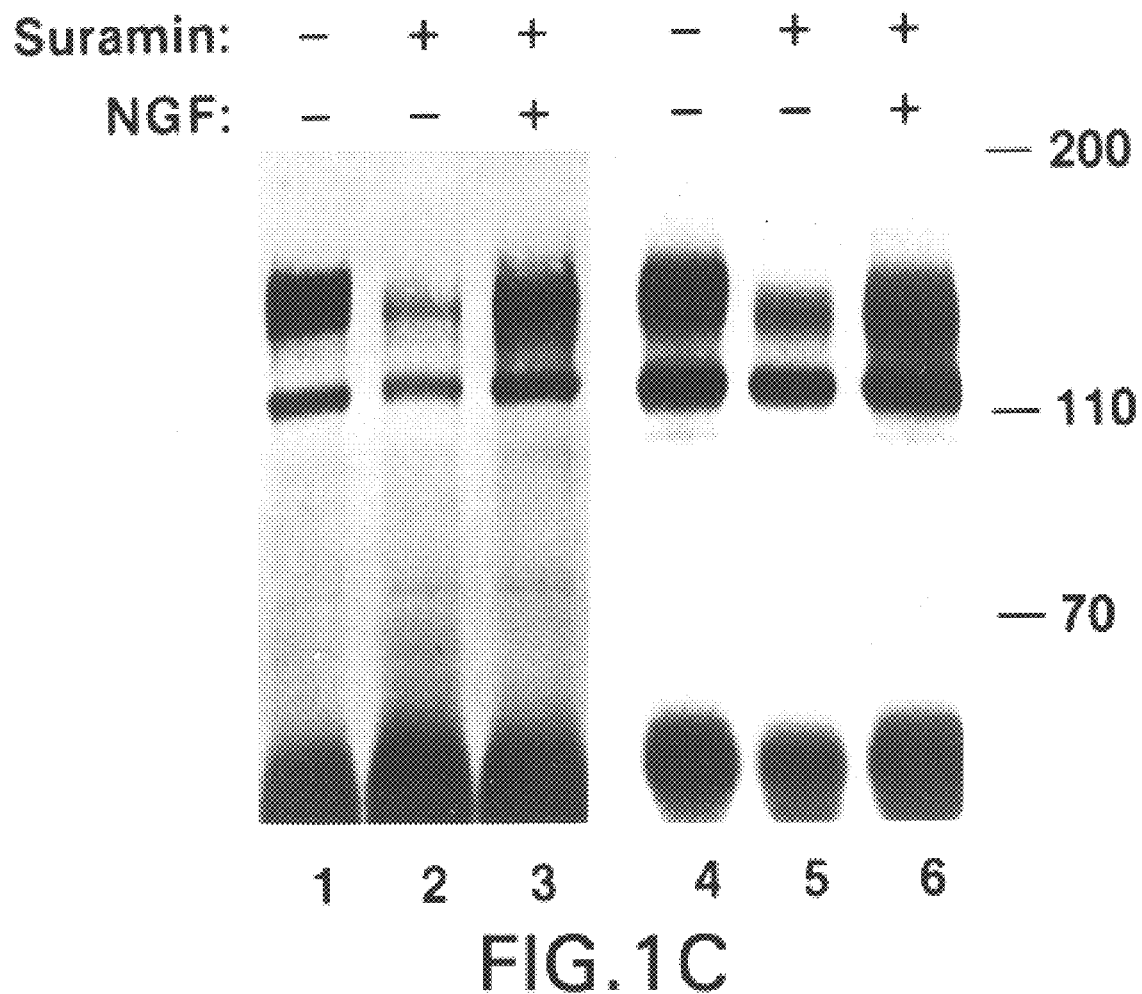

The stimulation of $gp140^{prototrk}$ tyrosine phosphorylation in response to NGF addition to PC12 cells is rapid, specific and occurs in the presence of physiological amounts of NGF. This previous study utilized immunoblotting analysis with phosphotyrosine (Ptyr) antibodies to detect tyrosine phosphorylation of $gp140^{prototrk}$. To determine if enhancement of serine or threonine phosphorylation of $gp140^{prototrk}$ are induced by NGF, and to compare the relative amounts of tyrosine, serine, and threonine phosphorylation, gPC12 cells were labeled with $^{32}$P-orthophosphate prior to NGF treatment and immunoprecipitation with antibodies to $gp140^{prototrk}$. $gp140^{prototrk}$ was phosphorylated predominately on serine residues in immunoprecipitates from untreated cells and cells treated with 50 ng/ml NGF for 5 min. The presence of NGF, however, stimulated the tyrosine phosphorylation of $gp140^{prototrk}$ 20-fold, although this represented less than 5% of the newly incorporated phosphate residues. In contrast, $p140^{prototrk}$ was labeled predominantly on tyrosine in immune complex kinase assays from NGF-treated PC12 cells or in $^{32}$P-labeled NIH-3T3 cells transfected with the rat trk gene (rtrk-3T3) (FIG. 1A). The tyrosine phosphorylation of $p140^{prototrk}$ expressed in NIH-3T3 cells was constitutive, apparently due to autocrine stimulation by NGF produced by these cells. Treatment of rtrk-3T3 cells with suramin, a polyanionic compound which inhibits and reverses the binding of some growth factors to their receptors (M. Hosang et al., J. Cell. Biochem. 29:265–273 (1985)), markedly reduced the tyrosine phosphorylation of $p140^{prototrk}$ in vivo and in immune complex kinase assays (FIG. 1B). When NGF was added to the suramin treated cells for 10 min, tyrosine phosphorylation of $gp140^{prototrk}$ observed in vivo and in vitro was stimulated at least 10-fold (FIG. 1C).

trk tyrosine phosphorylation occurred within one minute of NGF treatment cells, reached maximum levels after five minutes, and declined thereafter (FIG. 2A). Residual phosphorylation was detected after two days of treatment with NGF when the cell population was fully differentiated. trk tyrosine phosphorylation was also specific to NGF. Other peptide growth factors that elicit tyrosine phosphorylation in PC12 cells were tested in this assay (V. Hamburger and R. Levi-Montalcini, J. Exp. Zool. 111:457–502 (1949); I. B. Black et al., Growth Factors and Development, Current Topics in Developmental Biology, Vol. 24: (ed. Nilsen-Hamilton, M.) 161–192 1990)). EGF, basic FGF, insulin, and the phorbol ester PMA failed to induce trk as seen in cells treated with both basic FGF and NGF (FIG. 2B). It has been previously shown that these agents produce similar patterns of early responses in PC12 cells, including transcriptional activation of c-fos and c-myc (R. Levi-Montalcini and B. Booker, Proc. Natl. Acad. Sic. USA 46:384–391 (1960)). However, of these factors, only NGF and basic FGF stimulate neurite outgrowth.

To determine the minimal concentration of NGF capable of eliciting trk tyrosine phosphorylation, a dose response experiment was performed. Tyrosine phosphorylation was half maximal at 0.1 ng/ml NGF (50 pM) (FIG. 2C) indicating the trk phosphorylation occurs at physiologically relevant concentrations of NGF (S. Cohen, Proc. Natl. Acad. Sci. USA 46:302–311 (1960)).

Example 2

Expression of trk Gene in Embryonic Sensory Neural Crest-Derived Neurons

The trk gene is expressed in embryonic sensory neural crest-derived neurons including dorsal root ganglia (DRG) (FIGS. 3A–B and Martin-Zanca et al., (1990)). This expression is confined to neurons (note that the darkly staining glial cells are devoid of silver grains) and maintained in the adult.

To determine whether the trk protein in embryonic neurons was responsive to NGF, DRG from E13.5 and E14.5 mouse embryos were explanted, maintained in 50 ng/ml NGF on ice ≧10 mm., lysed, and subjected to trk antibody precipitation and anti-Ptyr immunoblotting analysis. As shown in FIG. 4A, phosphorylation of the $p145^{prototrk}$ was detectable in 14.5 day DRG but not in two independent preparations of 13.5 day DRG. Tyrosine phosphorylated trk protein was not detectable in the absence of exogenously administered NGF.

Dissection of DRG provides primarily the cell bodies and eliminates the axons, therefore the significance of these data with regard to timing and degree of $p145^{prototrk}$ activation should be interpreted with caution. The results in 14.5 DRG, however, determine that freshly dissected embryonic DRG neurons contain trk protein which is phosphorylated in response to NGF.

Example 3

NGF Stimulates $p140^{prototrk}$ Tyrosine Phosphorylation in Several trk-Expressing Cell Types To determine whether phosphorylation of $p140^{prototrk}$ in response to NGF was unique to rat PC12 cells or occurred in other NGF responsive cell lines, the state of the trk protein in additional neuroblastoma cell lines from different species was assayed. It was observed that $p140^{prototrk}$ tyrosine phosphorylation was also enhanced by NGF in the human neuroblastoma cell line LA-N-5 and in the murine cell line SY5Y (FIG. 4B). LA-N-5 and SY5Y cells express 4-fold less trk mRNA than PC12 cells, accounting for the lower amounts of tyrosine phosphorylated trk observed in these cell lines compared to PC12 cells.

Derivatives of the PC12 cell line have been generated by mutagenesis that have lost high affinity response to NGF (Bothwell et al. (1981)). One such line, NR18, lacks 75kNGF-R. Introduction of 75kNGF-R into these cells resulted in the reconstitution of biphasic Scatchard profile and at least partial function reconstitution (Hempstead et al. *J. Biol. Chem.* 265:9595–9598 (1990)). NR18 cells express the trk proto-oncogene at greatly reduced levels (Hempstead et al., (1991)).

The next procedure analyzed the phosphorylation state of the trk receptor on the NR18 cell line that has greatly reduced responsiveness to NGF (Bothwell et al., *Cell* 21:857–866 (1980)). Consistent with RNA expression data (Hempstead et al., (1991)) no phosphorylation of $p140^{prototrk}$ in response to NGF was observed in these cells (FIG. 4b). Thus, in NR18 cells, the tyrosine phosphorylation of $p140^{prototrk}$ correlates with the reduced ability of NGF to elicit a biological response.

Example 4

Trk Receptor Directly Binds to NGF

The above results, demonstrating the rapid phosphorylation of $p140^{prototrk}$ in several trk-expressing cell lines treated with NGF, suggested that the trk receptor might directly bind NGF. To determine if NGF was capable of binding to $p140^{prototrk}$, several cell lines were analyzed for the ability of trk-specific antisera to precipitate receptor-ligand complexes in affinity crosslinking experiments (FIG. 5). The cell lines assayed were rat PC12, human LA-N-5, mouse SY5Y, mouse NIH-3T3, mouse rtrk-3T3, and human AB75 cells. NGF induces the tyrosine phosphorylation of $p140^{prototrk}$ in PC12, LA-N-5, SY5Y, and rtrk-3T3, but not in AB75 melanoma or NIH-3T3 cells which express no detectable trk messenger RNA. $^{125}$I-labeled NGF was crosslinked to cells using the lipophilic photoaffinity agent HSAB. Previous studies with this crosslinking agent have shown that in PC12 cells and sympathetic neurons, two NGF containing species of 100 kDa and 150–160 kDa are observed (J. Massague et al., *J. Biol. Chem.* 256:9419–9424 (1981); Hempstead, et al. (1990); S. O. Meakin and E. M. Shooter, *Neuron* 6:153–163 (1991)). The 100 kDa species represents $^{125}$I-NGF bound to 75kNGF-R (M. Hosang and E. M. Shooter, *J. Biol. Chem.* 260:655–662 (1985)). Following crosslinking, the cells were washed to remove unbound $^{125}$I-NGF, lysed in detergent, and the lysates incubated with antibodies (FIG. 5). It was observed that the 160 kDa species is present in anti-NGF or anti-$p140^{prototrk}$ immunoprecipitates from PC12 and rtrk-3T3 cells and not in A875 or NIH3T3 cells. The immunoprecipitation of the 160 kDa species was blocked by addition of a trk-derived peptide used to generate the antibody, and was not seen if excess unlabeled NGF was added to the $^{125}$I-NGF treated cells prior to crosslinking. A 160 kDa crosslinked product was also observed in LA-N-5 and SY5Y cells. The crosslinked 100 kDa species was present in PC12 and A875 cells and not in the 3T3 cell lines, reflecting the absence of expression of the 75kNGF-R in NIH-3T3 cells. The above experiments establish that NGF binds to $p140^{prototrk}$ and that this binding is seen only in cell lines which show $p140^{prototrk}$ tyrosine phosphorylation in response to NGF.

Of equal importance to the demonstration of binding, it is essential to determine whether the affinity of binding reflects physiologically relevant conditions. Scatchard plot analysis was carried out to determine that affinity of NGF for $p140^{prototrk}$ expressed in NIH-3T3 cells. Crude membranes were prepared from cells and assayed by binding to $^{125}$I-NGF. Membranes obtained from rtrk-3T3 cells displayed a linear Scatchard plot with a $K_d$ of approximately $10^{-9}$M (FIGS. 6A–B). By this analysis, the number of receptors was approximately 200,000–500,000/cell.

Example 5

Expression of trk or trk-Related Messenger RNA in Several Cell Types

The trk gene is a member of a gene family of TK receptors that includes the related gene trkb. To determine if trk is transcribed in PC12 cells, the expression of trk transcripts was assayed by Northern transfer analysis with a full-length trk cDNA probe (R. Klein et al., (1990a)). PC12 cells contained trk transcripts (FIG. 7). The level of trk transcripts was not affected by the addition of NGF. To determine whether additional trk-related genes were transcribed in PC12 cells, mRNA was hybridized at low stringency with the highly conserved trk TK domain. trk transcripts have been found in LA-N-5 cells, Sy5y cells and DRG from 13.5 day or 14.5 day embryonic mice.

Example 6

Generation of Heterologous Fibroblast Cell Lines that Express trkB cDNA

The strong relatedness between trkB and trk sequences suggested that these two receptors might bind either identical or related ligands. Previous experiments with NGF and trk were greatly facilitated by the existence of tumor cell lines of neuronal origin that responded physiologically to the administration of NGF and which expressed the trk receptor (Kaplan et al., (1991); Hempstead et al., (1991)). In the absence of such existing cell lines, to test whether, like trk, the trkB receptor became phosphorylated on tyrosine residues upon exposure to neurotrophic factors, it was necessary to generate heterologous fibroblast cell lines expressing a full length trkB cDNA that encodes a functional tyrosine kinase receptor.

NIH 3T3 cells, which do not normally express any trk family genes (Kaplan et al., (1991)), were transfected with a 4.8 kb MSV LTR-driven rat trkB cDNA (Middlemas et al., (1991)) (pJM8) using calcium phosphate coprecipitation, together with a neo-selectable plasmid (Parada et al., (1984)). G418-resistant colonies were isolated, expanded, and screened for the expression of trkB transcripts and protein and the absence of any additional trkB transcripts and protein and the absence of any additional trk-related transcripts.

Northern transfer analysis using a trkB specific (extracellular domain) probe confirmed the expression of the predicted size transcript in several of the trkB-transfected NIH-3T3 G418-resistant cell lines. To rule out the possibility that expression of endogenous trk-related genes might be induced in the NIH 3T3 transfected cells in response to the presence of an exogenous trkB gene, hybridization to RNAs from these cell lines with a trk-specific probe or with a trk tyrosine kinase domain probe (at reduced stringency) was performed. Under these conditions no additional transcripts other than those corresponding to the transfected trkB cDNA were detected.

The trkB transfected G418-resistant cell lines were next examined for the expression of the rat cDNA-encoded trkB protein. Cell lysates were prepared, precipitated with wheat germ agglutinin to enrich for glycoproteins, transferred to nitrocellulose, and probed with an anti-peptide antibody directed against the extracellular domain of the trkB protein. FIG. 8 shows examples of this procedure where a protein of the expected size (145 kDa) is present in lanes designated pJM8-3 and pJM8-5. Thus, the transfected rat trkB cDNA was approximately expressed in NIH 3T3 cells and a glycoprotein of the predicted size (145 kDa) was detected with anti-trkB antibodies. Growth factor stimulation, cross-linking assays and Scatchard analysis were performed with multiple independent cell lines.

Example 7

The trkB Gene Product is Not Phosphorylated on Tyrosine in Response to NGF

The product of the trk proto-oncogene (gp140$^{proto-trk}$) is tyrosine phosphorylated in response to NGF in PC12 cells, NGF-responsive neuroblastoma cells, heterologous fibroblasts and Xenopus oocytes (Kaplan et al., (1991); A. R. Nebreda et al., Science 252:558–560 (1991); Klein et al., (1991)). Next it was examined whether NGF elicited tyrosine phosphorylation of gp145$^{trkB}$ in trkB-expressing NIH 3T3 cells. Cell line pJM8-3 was treated with high concentrations of NGF (100 ng/ml) for 5 minutes. The cells were lysed, immunoprecipitated with anti-trkB antiserum 443, transferred to nitrocellulose filters and probed with anti-phosphotyrosine (α-Ptyr) antibodies. As a negative control, untransfected NIH-3T3 cells were treated in parallel, while PC12 cells were used as a positive control for NGF responsiveness (Kaplan et al., (1991)). As previously shown, the trk receptor (gp140$^{prototrk}$) is phosphorylated in PC12 cells upon addition of NGF (FIG. 9) while no increase in phosphorylation of the trkB receptor was detected even at the high NGF levels employed. These results indicate that, unlike gp140$^{proto-trk}$, the tyrosine kinase encoded by the trkB gene is not activated by NGF, suggesting that gp145$^{trkB}$ is not a receptor for NGF.

Example 8 trkB Receptor Directly Binds to NT-3

To detemine whether trk related receptors with strong structural similarity to trk would be receptors for structurally related neurotrophins to NGF, the following study was performed.

The structure and sequence of the trkB receptor, and its neural-specific expression profile have strong parallels to that of trk. Therefore, the rapid tyrosine phosphorylation of trkB in response to the physiological doses of NT-3 can be interpreted to indicate that trkB is the functional receptor for NT-3. The BDNF result is less certain since high levels (perhaps higher than physiologically relevant) were necessitated to stimulate trkB phosphorylation. Alternatively, a subunit of the functional BDNF receptor that increases affinity response to BDNF may be absent in these assays.

What follows is a description of the reagents generated by Applicants and used to perform these experiments. The BDNF used in Applicants' preliminary experiments was prepared from human blood platelets as described by Gurney et al. The NT-3 was provided as a Cos-cell extract.

To study the expression of trkB in transfected cell lines, full length trkB cDNAs were cloned into CMV and MuLV LTR expression vectors and transfected into NIH-3T3 fibroblasts, PC 12 pheochromocytoma cells and NR18 cells (a derivative of PC12 cells). Stable G418 resident clones were picked and expanded. Assays to detect cell lines expressing trkB were performed by detergent lysis of the cells, followed by WGA-sepharose adsorption. The adsorbed material was analyzed by SDS-PAGE on 7.5% gels, transferred to nitrocellulose and probed with antisera 442, a trkB specific rabbit antisera. The Western blots contained a WGA-sepharose extract of mouse brain as a control and BIORAD prestained molecular weight standards (200, 116, 80 and 43 kDa).

NIH-3T3 fibroblasts were transfected with constructs pJM8-1 through pJM8-6. Expression of trkB was detected in 3T3 cells transfected with pJM8-2, pJM2-3, pJM8-4, pJM8-5 and pJM8-6.

NR18 cell lines were transfected with the following constructs: pJM9-1 through pJM9-16, pJM11-1, pJM11-4 through pJM11-16, pJM13-1 through pJM13-29, pJM9-18 and pJM9-19. NR18 cells transfected with several of these constructs showed expression of trkB as detected by Western blot (e.g., pJM9-2, pJM9-4, pJM9-11 and pJM9-11).

To study growth factor stimulation in cells transfected with trkB, NIH 3T3 trk transfected 3T3 (pJM7-23), trkB transfected 3T3 cells (pJM8-3) and non-transfected 3T3 cells (control cells) were exposed to media or media containing 100 μl/ml of NGF-COS cell supernatant, 100 μl/ml NT-3 COS cell supernatant, 5 μl/ml human platelet extract, or 50 μl/ml human platelet extract, for 10 minutes at 37° C. The plates were rinsed, lysed, and the trk or trkB was immunoprecipitated with rabbit antisera 443 and protein A Sepharose in the presence or absence of 10 μg/ml blocking peptide. After washing, the beads were denatured in sample buffer, the proteins were separated on a 7.5% gel and transferred to nitrocellulose. The blots were blocked with 2% BSA and probed with an antiphosphotyrosine monoclonal antibody (4G10). After binding of alkaline phosphateconjugated rabbit-anti-mouse antibody, the blots were washed and developed with BCIP and NBT. Experimental results revealed basal expression, however, trk-expressing 3T3 cells were stimulated only by NGF and trkB-expressing 3T3 cells were stimulated only by NT-3.

Example 9

BDNF and NT-3 Specifically Stimulate Tyrosine Phosphorylation of p145$^{trkB}$

BDNF and NT-3 are neurotrophic factors that display many functional and structural features that are reminiscent of NGF. The genes encoding BDNF and NT-3 have recently been cloned and used to express high levels of the biologically active factors in pure form (A. Rosenthal et al., *Neuron* 4:773 (1990)). It was tested whether these NGF-related neurotrophic factors would stimulate phosphorylation of the trkB glycoprotein by exposing the pJM-8 cell lines to 100 ng/ml of NGF, BDNF, or NT-3 (~4 nM) for 5 minutes. The cells were then lysed and the lysates incubated with a trkB anti-peptide antiserum (443) with or without excess peptide. After transfer to nitrocellulose filters, the trkB proteins were probed with an anti-phosphotyrosine (α-ptyr) monoclonal antibody (FIG. 10) (Kaplan et al. (1991)). While addition of NGF had no detectable effect on the degree of tyrosine phosphorylation of gp145$^{proto-trkB}$, administration of either NT-3 or BDNF resulted in a strong phosphorylation of gp145$^{proto-trkB}$ on tyrosine as determined by immunoblotting with α-ptyr antibody (mAb4G10). Thus, both neurotrophic factors NT-3 and BDNF can elicit tyrosine phosphorylation of gp145$^{trkB}$ in a manner similar to that observed for NGF stimulation of the trk receptor. Similar results have been obtained with NT-3 and BDNF in Rat2 cells expressing trkB.

Having detected gp145$^{trkB}$ phosphorylation in response to BDNF and NT-3, it was next determined whether unrelated polypeptide growth factors were capable of eliciting a similar response. Platelet-derived growth factor (PDGF; 100 ng/ml), epidermal growth factor (EGF; 100 ng/ml), insulin (100 ng/ml), and basic fibroblast growth factor (bFGF; 100 ng/ml), and basic fibroblast growth factor (bFGF; 100 ng/ml) were added independently to exponentially growing cultures of pJM8-3 cells. No tyrosine-phosphorylated gp145$^{trkB}$ was detected with these growth factors under conditions identical to those used for the BDNF and NT-3 studies (FIG. 11). These data further confirm the specificity of the gp145B$^{trkB}$ response to the neurotrophic factors BDNF and NT-3.

The previous studies were done in the presence of high concentrations of neurotrophic factors. Dose response experiments were next performed to determine the range of concentrations at which phosphorylation of the trkB receptor was stimulated by NT-3 or BDNF. Cells were incubated with quantities of NT-3 or BDNF ranging from 0.1 ng/ml to 250 ng/ml and treated as described in FIG. 12. The results from these studies show that gp145$^{trkB}$ is phosphorylated maximally by 50 ng/ml of either NT-3 or BDNF and that half-maximal response was obtained with concentrations on the order of 5 to 10 ng/ml (300–600 pM) (FIG. 12). Thus, the trkB receptor, gp145$^{trkB}$, is phosphorylated on tyrosine residues upon exposure to physiological concentrations of either of the two neurotrophic factors, NT-3 or BDNF.

In PC12 cells, trk tyrosine phosphorylation appears rapidly (1 minute) after NGF administration (Kaplan et al., (1991)). The time course of gp145$^{trkB}$ phosphorylation observed with NT-3 and BDNF was similar to that previously observed for the trk/NGF complex. Tyrosine phosphorylation of trkB was detected within one minute of NT-3 or BDNF addition and maximal levels were reached by 5 minutes (FIG. 14).

Example 10

BDNF and NT-3 Do Not Have Synergistic Effects on gp145$^{trkB}$ Phosphorylation

The surprising finding that two members of the NGF-related neurotrophic family, NT-3 and BDNF, but not NGF, could induce trkB tyrosine phosphorylation raised the possibility that NT-3 and BDNF might interact in some manner to either stimulate or attenuate the phosphorylation of trkB. It was determined whether addition of NT-3 and BDNF together at levels below the half maximal dose (5–10 ng/ml; see FIG. 13), had any synergistic effects on the tyrosine phosphorylation of gp145$^{trkB}$. No interaction effects (enhancement or reduction of phosphorylation) were observed between NT-3 and BDNF in the phosphorylation assay.

While the foregoing invention has been described in some detail for purposes of clarity and understanding, it will be appreciated by one skilled in the art from a reading of this disclosure that various changes in form and detail can be made without departing from the true scope of the invention.

What is claimed is:

1. A method of detecting a neurotrophic factor with reference to a control, comprising the steps of:

a) bringing cells that express a trkB-proto-oncogene receptor protein into contact with a putative neurotrophic factor, wherein the contact is effected under conditions such that binding of the neurotrophic factor to and subsequent activation of the receptor protein can occur;

b) determining an amount of tyrosine phosphorylation of trkB-proto-oncogene receptor protein effected by step (a); and c) comparing the amount of phosphorylation determined by step (b) with that of a control trkB-proto-oncogene receptor protein which is not contacted with the putative neurotrophic factor, whereby an increase in the amount of phosphorylation relative to that of the control detects a neurotrophic factor.

2. The method of claim 1, further comprising, prior to step (a), the step of bringing the cells into contact with orthophosphate, and in step (b), contacting trkB-proto-oncogene receptor protein with anti-trkB antibody to effect immunoprecipitation and measuring the amount of 3-orthophosphate incorporated in immunoprecipitated trkB-proto-oncogene receptor protein, whereby the measuring determines an amount of tyrosine phosphorylation of trkB-proto-oncogene receptor protein effected by step (a).

3. A method of detecting trk-proto-oncogene receptor protein in a sample, comprising the steps of:

a) contacting nerve growth factor with a biological sample suspected of containing trk-proto-oncogene receptor protein, wherein the contacting is effected under conditions such that binding between nerve growth factor and trk-proto-oncogene receptor protein can occur; and b) detecting tyrosine phosphorylation in the sample of step (a), whereby the detection of tyrosine phosphorylation as compared to the absence of tyrosine phosphorylation in the sample in the absence of nerve growth factor indicates the presence of trk-proto-oncogene receptor protein in the sample.

4. The method of claim 3, further comprising the steps of:

(i) after step (a), contacting the sample with an antibody specific for nerve growth factor; and (ii) immunoprecipitating the nerve growth factor.

\* \* \* \* \*